(12) United States Patent
Lai

(10) Patent No.: US 7,205,368 B2
(45) Date of Patent: Apr. 17, 2007

(54) S-(α, α'-DISUBSTITUTED-α'-ACETIC ACID) SUBSTITUTED DITHIOCARBONATE DERIVATIVES FOR CONTROLLED RADICAL POLYMERIZATIONS, PROCESS AND POLYMERS MADE THEREFROM

(75) Inventor: John Ta-Yuan Lai, Broadview Heights, OH (US)

(73) Assignee: Noveon, Inc., Cleveland, OH (US)

(*) Notice: Subject to any disclaimer, the term of this patent is extended or adjusted under 35 U.S.C. 154(b) by 424 days.

(21) Appl. No.: 10/278,335

(22) Filed: Oct. 23, 2002

(65) Prior Publication Data

US 2003/0120101 A1 Jun. 26, 2003

Related U.S. Application Data

(63) Continuation-in-part of application No. 09/505,749, filed on Feb. 16, 2000, now Pat. No. 6,596,899.

(51) Int. Cl.
*C08F 28/02* (2006.01)
*C07C 315/00* (2006.01)
*C07C 321/00* (2006.01)
*C07C 327/00* (2006.01)

(52) U.S. Cl. ............... 526/286; 588/230; 562/426; 562/581

(58) Field of Classification Search ........... 562/426, 562/581; 526/286; 558/243, 230
See application file for complete search history.

(56) References Cited

U.S. PATENT DOCUMENTS

| | | | |
|---|---|---|---|
| 3,285,945 A | 11/1966 | Wember | |
| 3,285,949 A | 11/1966 | Siebert | |
| 3,770,698 A | 11/1973 | Riew | |
| 3,928,491 A | 12/1975 | Waters | |
| 3,992,432 A | 11/1976 | Napier et al. | |
| 4,769,419 A | 9/1988 | Dawdy | |
| 5,055,515 A | 10/1991 | Backderf | |
| 5,140,068 A | 8/1992 | Siebert et al. | |
| 5,157,077 A | 10/1992 | Siebert et al. | |
| 5,198,510 A | 3/1993 | Siebert et al. | |
| 5,258,445 A | 11/1993 | Sperk, Jr. et al. | |
| 5,280,068 A | 1/1994 | Siebert et al. | |
| 5,312,956 A | 5/1994 | Bertsch | |
| 5,385,963 A | 1/1995 | McBain et al. | |
| 6,153,705 A | 11/2000 | Corpart et al. | |
| 6,380,335 B1 | 4/2002 | Charmot et al. | |
| 6,395,850 B1 | 5/2002 | Charmot et al. | |

FOREIGN PATENT DOCUMENTS

| | | | |
|---|---|---|---|
| GB | 1223524 | * 2/1971 | |
| WO | 98/01478 | 1/1998 | |
| WO | 99/05099 | 2/1999 | |
| WO | 99/31144 | 6/1999 | |
| WO | 99/35177 | 7/1999 | |

OTHER PUBLICATIONS

World Polymer Congress, 37th International Symposium on Macromolecules, Jul. 12-17, 1998, Gold Coast, Australia.
"Living Free-Radical Polymerization by Reversible Addition-Fragmentation Chain Transfer: The RAFT Process", John Chiefari, et al., CSIRO *Molecular Science, Bag 10*, Clayton South. Clayton, Victoria 3169, Australia, Received Mar. 27, 1998, Revised Manuscript Received Jun. 10, 1998.
"The Synthesis of Organic Trethiocarbonates[1]", H.C. Godt, Jr., and R.E. Wann, *Journal of Organic Chemistry*, 26, 4047 (1961).
"Phase-Transfer Synthesis of Symmetrical and Unsymmetrical Dialkyl Trithiocarbonates", Iacopo Degani, et al, Synthesis, p. 894 (1986).
"A New Form of Controlled Growth Free Radical Polymerization", Julia Kristina, et al., CSIRO, Division of Chemicals and Polymers, *Macromol, Symp.* III, 13-23 (1996).
"One Pot Phase Transfer Synthesis of Trithiocarbonates from Carbon Disulphide and Alkyl Halides", Albert W.M. Lee, et al, *Synthetic Comm.* 18(13), 1531 (1988).
"A Novel One-step Synthesis of Symmetrical Dialkyl Trithiocarbonates", Man-kit Leung, et al, *Journal of Chemical Research* (S), 1995, 478-479.
"Direct Synthesis of Double Hydrophilic Statistical di- and Triblock Copolymers Comprised of Acrylamide and Acrylic Acid Units via the MADIX Process", Daniel Taton, et al, Macromol, Rapid Commun, 22, No. 18, 1497-1503 (2001).
"Dithiocarbamates as universal reversible addition-fragmentation chain transfer agents", M. Destarac, et al, Macromol. Rapid Commun., 21, No. 15, 1035-1039(2000).
"Living Radical Polymerization with Reversible Addition—Fragmentation Chain Transfer (RAFT Polymerization) Using Ditriocarbamates as Chain Transfer Agents", Roshan T.A. mayadunne, et al., Macromolecules 1999, 32, 6977-6980.

* cited by examiner

*Primary Examiner*—Taylor Victor Oh
(74) *Attorney, Agent, or Firm*—Thoburn T. Dunlap; Joe A. Powell

(57) ABSTRACT

Dithiocarbonate derivatives are disclosed, along with a process for preparing the same. The dithiocarbonate compounds can be utilized as initators, chain transfer agents and/or terminators in controlled free radical polymerizations. The dithiocarbonates can be used to produce polymers having narrow molecular weight distribution. Advantageously, the compounds of the present invention can also introduce functional groups into the resulting polymers. The dithiocarbonate compounds have low odor and are substantially colorless.

24 Claims, No Drawings

S-(α, α'-DISUBSTITUTED-α' '-ACETIC ACID) SUBSTITUTED DITHIOCARBONATE DERIVATIVES FOR CONTROLLED RADICAL POLYMERIZATIONS, PROCESS AND POLYMERS MADE THEREFROM

CROSS REFERENCE

This patent application is a continuation-in-part application based on U. S. application Ser. No. 09/505,749 filed Feb. 16, 2000 for S,S'-Bis-(α, α'-Disubstituted-α''-Acetic Acid)-Trithiocarbonates And Derivatives As Initiator-Chain Transfer Agent-Terminator For Controlled Radical Polymerizations And The Process For Making The Same, now U.S. Pat. No. 6,596,899.

FIELD OF THE INVENTION

The present invention relates to s,s'-bis-(α, α'-disubstituted-α''-acetic acid)-trithiocarbonates and derivatives thereof, as well as a process for making the same. Moreover, other functional end groups can be derived from the carboxylic acid end groups. The compounds can be utilized as initiators, chain transfer agents, or terminators for controlled free radical polymerizations. Free radical polymerizations utilizing s,s'-bis-(α,α'-disubstituted-α''-acetic acid)-trithiocarbonate compounds generally form telechelic polymers. If an initiator other than the s,s'-bis-(α,α'-disubstituted-α''-acetic acid)-trithiocarbonate compound is also utilized, a polymer having a single functional end group is formed in proportion to the amount of the initiator to the s,s'-bis-(α, α'-disubstituted-α''-acetic acid)-trithiocarbonate compound utilized.

In a further embodiment, dithiocarbonate derivatives are disclosed, along with a process for preparing the same. The dithiocarbonate compounds can be utilized as initators, chain transfer agents and/or terminators in controlled free radical polymerizations. The dithiocarbonates can be used to produce polymers having narrow molecular weight distribution. Advantageously, the compounds of the present invention can also introduce functional groups into the resulting polymers. The dithiocarbonate compounds have low odor and are substantially colorless.

BACKGROUND OF THE INVENTION

Although several members of the class of organic thiocarbonates have been known for many years and various routes have been employed for their synthesis, the s,s'-bis-(α,α'-disubstituted-α''-acetic acid)-trithiocarbonate compounds of the present invention have not been disclosed. Trithiocarbonate compounds have been claimed for various applications, such as pesticides for agriculture, and also as lubricating oil additives.

Traditional methods of producing block copolymers, such as by living polymerization or the linking of end functional polymers, suffer many disadvantages, such as the restricted type monomers which can be utilized, low conversion rates, strict requirements on reaction conditions, and monomer purity. Difficulties associated with end linking methods include conducting reactions between polymers, and problems of producing a desired pure end functional polymer. The s,s'-bis-(αα'-disubstituted-α''-acetic acid)-trithiocarbonate compounds of the present invention can alleviate the above noted problems and difficulties when utilized in free radical polymerizations.

The prior art WO98/01478 reference discloses the use of thiocarbonates to conduct living free radical polymerizations. The reference is limited to alkyl and benzyl functional groups, and is unable to make any aryl or carboxylic acid substituted trithiocarbonates with general methods known to the art. *Synthesis*, p 894 (1986), *J. Chemical Research* (Synopsis), p 478 (1995), and *Synthetic Communications*, Vol. 18, p 1531 (1988). We have also found the conversion for the dibenzyl derivatives disclosed in their example 26 to be very slow compared to the present invention when polymerizing acrylate, as can be seen in the Example section of this application. The WO/01478 reference states in the background that experiments have shown that dithiocarbamate derivatives have low transfer constants and are substantially ineffective in conferring living characteristics to radical polymerizations.

*Macromolecules*, 32, p 6977–6980 (1999) states that

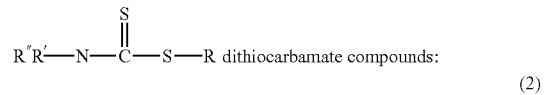

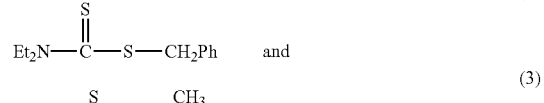

cannot control polymerization and are not effective RAFT agents. Additionally, carboxyl end groups cannot be formed utilizing the processes disclosed. Also WO 99/35177 and Macromolecules, Rapid Communications, 21, p 1035–1039 (2001) finds that R, $R^1$, and $R^2$ need to be fine tuned to control polymerization, meaning there is no guarantee all dialkyl dithiocarbamate will work as RAFT agents. Moreover, the substituent of the single bonded sulfur atom cannot be a carboxylic acid containing group in their synthesis.

U.S. Pat. No. 6,153,705 relates to a process for polymerizing block polymers of general formula (I):

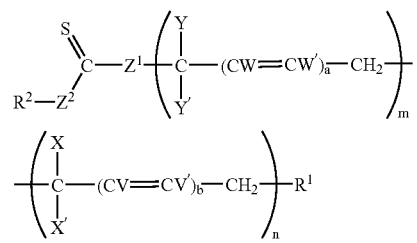

in which process the following are brought into contact with each other:

an ethylenically unsaturated monomer of formula:

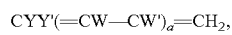

a precursor compound of general formula (II):

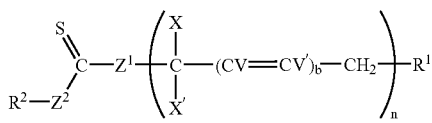

and a radical polymerization initiator.

Macromolecule Rapid Communications 2001, 22, p 1497–1503 and U.S. Pat. No. 6,153,705 disclose various xanthate compounds. The references cannot prepare the xanthate compounds of the present invention utilizing the methods disclosed within the references. 1) Alkylation with tertiary alkyl halides disclosed in the '705 patent will result in elimination, not substitution. The α-halo-α', α"-dialkylacetic acid disclosed by the reference cannot be alkylated. 2) The compounds of the present invention contain a tertiary carbon attached to the single bonded sulfur atom of the compound. The '705 patent preferably utilizes an $R^1$ group having a secondary carbon atom which results in a lower chain transfer coefficient than the present invention. Moreover, the xanthates disclosed by the references have been found to be less effective.

Unexpectedly, in view of the prior art, the compounds of the present invention are able to confer living characteristics to a free radical polymerization.

SUMMARY OF THE INVENTION

The present invention relates to s,s'-bis-(α,α'-disubstituted-α"-acetic acid)-trithiocarbonates which have the general formula:

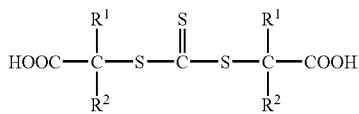

where $R^1$ and $R^2$ are set forth below, to derivatives thereof, and to a process for making the same.

The s,s'-bis-(α,α'-disubstituted-α"-acetic acid) trithiocarbonate compounds can generally be formed from carbon disulfide, a haloform, and a ketone in a strong base, such as sodium hydroxide, followed by acidification. The s,s'-bis-(α,α'-disubstituted-α"-acetic acid) trithiocarbonate compounds can be used as inifertors, i.e. as initiators and chain transfer agents, and/or chain terminators or as a chain-transfer agent during polymerization. The compounds can thus be utilized to control free radical polymerization thermally and chemically to give narrow molecular weight distributions. Polymerization of monomers can be in bulk, in emulsion, or in solution. Block copolymers can be made if two or more monomers are polymerized in succession. The difunctional acid end groups present can further react with other reactive polymers or monomers to form block or random copolymers. Free radical polymerizations utilizing the s,s'-bis-(α,α'-disubstituted-α"-acetic acid)-trithiocarbonate compounds generally form telechelic polymers. If an initiator other than the s,s'-bis-(α,α'-disubstituted-α"-acetic acid)-trithiocarbonate compound is also utilized, a polymer having a single functional end group is formed in proportion to the amount of said other initiator to the s,s'-bis-(α,α'-disubstituted-α"-acetic acid)-trithiocarbonate compound utilized.

In a further embodiment, dithiocarbonate compounds of the present invention have the general formula:

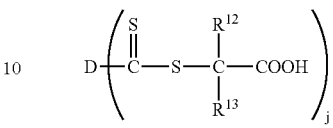

wherein D, $R^{12}$, $R^{13}$ and j are defined hereinbelow. Preferably, the substituent D is an alkoxy or an amine derivative, preferably a dialkylamino derivative, and thus, the dithiocarbonate compounds are xanthate and dithiocarbamate derivatives. A process for preparing the dithiocarbonate compounds is disclosed.

The dithiocarbonate compounds can be utilized as chain transfer agents in free radical polymerizations, as well as initiators and/or chain terminators. Narrow molecular weight distribution polymers can advantageously be produced with the dithiocarbonates of the present invention. The polymers formed in the presence of the dithiocarbonate compounds have at least one terminal carboxyl group which can be further reacted to form block or random copolymers. The monomers or polymers polymerized onto the dithiocarbonate compounds are added between the single bonded sulfur atom and the adjacent tertiary carbon atom. The polymerizations are conducted under inert atmospheres. The compounds and/or the polymers or copolymers of the present invention can be made water soluble or water dispersible through their metal or ammonium salts of the carboxylic acid group.

Accordingly, polymers having the following formula can be produced utilizing the dithiocarbonate compounds of the present invention:

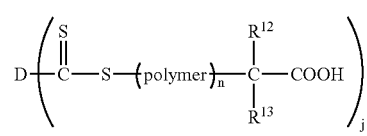

wherein, D, $R^{12}$, $R^{13}$, polymer, j and n are defined hereinbelow.

DETAILED DESCRIPTION OF THE INVENTION

The s,s'-bis-(α,α'-disubstituted-α"-acetic acid)-trithiocarbonate and derivatives prepared by the processes disclosed later herein generally can be described by the formula:

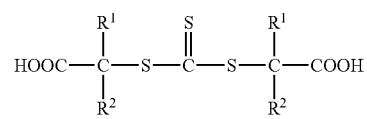

wherein $R^1$ and $R^2$, independently, can be the same or different, and can be linear or branched alkyls having from 1 to about 6 carbon atoms, or a $C_1$ to about $C_6$ alkyl having one or more substituents, or one or more aryls or a substituted aryl group having 1 to 6 substituents on the aryl ring, where the one or more substituents, independently, comprise an alkyl having from 1 to 6 carbon atoms; or an aryl; or a halogen such as fluorine or chlorine; or a cyano group; or an ether having a total of from 2 to about 20 carbon atoms such as methoxy, or hexanoxy; or a nitro; or combinations thereof. Examples of such compounds include s,s'-bis-2-methyl-2-propanoic acid-trithiocarbonate and s,s'-bis-(2-phenyl-2-propanoic acid)-trithiocarbonate. $R^1$ and $R^2$ can also form or be a part of a cyclic ring having from 5 to about 12 total carbon atoms. $R^1$ and $R^2$ are preferably, independently, methyl or phenyl groups.

The abbreviated reaction formula for the s,s'-bis-(α,α'-disubstituted-α"-acetic acid)-trithiocarbonates of the present invention can be generally written as follows:

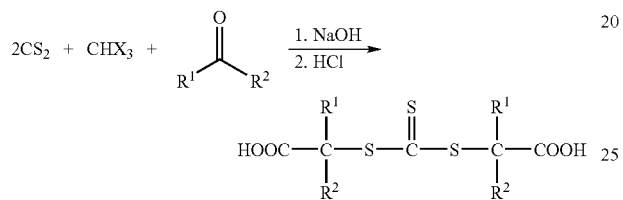

The process utilized to form the s,s'-bis-(α,α'-disubstituted-α"-acetic acid)-trithiocarbonate compounds of the present invention is generally a multi-step process and includes combining the carbon disulfide and a base whereby an intermediate trithio structure is formed, see I, II, III, and IV. Ketone can serve as solvent for the carbon disulfide/base reaction and thus can be added in the first step of the reaction. In the second step of the reaction, the haloform, or haloform and ketone, or a α-trihalomethyl-α-alkanol are added to the trithio intermediate mixture and reacted in the presence of additional base, see V, VI, and VII. The formed reaction product, see IX, is subsequently acidified, thus completing the reaction and forming the above described s,s'-bis-(α,α'-disubstituted-α"-acetic acid)-trithiocarbonate compound, see X.

The reaction is carried out at a temperature sufficient to complete the interaction of the reactants so as to produce the s,s'-bis-(α,α'-disubstituted-α"-acetic acid)-trithiocarbonate compound in a desired time. The reaction can be carried out at any temperature within a wide range from about the freezing point of the reaction mass to about the reflux temperature of the solvent. The reaction temperature is generally from about minus 15° C. to about 80° C., desirably from about 0° C. to about 50° C., and preferably from about 15° C. to about 35° C., with room temperature being preferred. The reaction can be performed at atmospheric pressure. The reaction time depends upon several factors, with the temperature being most influential. The reaction is generally complete within 20 hours and preferably within 10 hours.

A phase transfer catalyst is preferably utilized if a solvent is used in the reaction. Examples of solvents are set forth herein below. The ketone utilized in the reaction may double as a solvent, and therefore no catalyst usually is needed. The amount of phase transfer catalyst, when utilized in the present invention, is generally from about 0.1 mole percent to about 10 mole percent, desirably from about 0.5 mole percent to about 5 mole percent and preferably from about 2 mole percent to about 4 mole percent per mole of carbon disulfide. The phase transfer catalysts can be polyether, and/or an onium salt including a quaternary or tertiary organic compound of a group VA or VIA element of the Periodic Table and salts thereof. Most preferred are quaternary amines, and salts thereof.

"Onium salts" more particularly refer to tertiary or quaternary amines and salts such as are generally used in the phase transfer catalysis of heterogeneous reaction in immiscible liquids. The general requirement for the onium salt chosen is that it be soluble in both the organic and aqueous phases, when these two liquid phases are present, and usually a little more soluble in the organic phase than the aqueous phase. The reaction will also proceed with a phase transfer catalyst when there is only a single organic liquid phase present, but such a reaction is less preferable than one in which both aqueous and organic liquid phases are present. A wide variety of onium salts is effective in this ketoform synthesis.

The onium salts include the well-known salts, tertiary amines and quaternary compounds of group VA elements of the Periodic Table, and some Group VIA elements such as are disclosed in the U.S. Pat. No. 3,992,432 and in a review in Angewandte Chemie, International Edition in English, 16 493–558 (August 1977). Discussed therein are various anion transfer reactions where the phase transfer catalyst exchanges its original ion for other ions in the aqueous phase, making it possible to carry our chemistry there with the transported anion, including OH-ions.

The onium salts used in this synthesis include one or more groups having the formula $(R_nY)^+X^-$, wherein Y is either a pentavalent ion derived from an element of Group VA, or a tetravalent ion derived from an element of Group VIA; R is an organic moiety of the salt molecule bonded to Y by four covalent linkages when Y is pentavalent, and three covalent linkages when Y is tetravalent; $X^-$ is an anion which will dissociate from the cation $(R_nY)^+$ in an aqueous environment. The group $(R_nY)^+ X^-$ may be repeated as in the case of dibasic quaternary salts having two pentavalent Group VA ions substituted in the manner described.

The preferred onium salts for use in the invention have the formula $(R^AR^BR^CR^DY^+)X^-$ wherein Y is N or P, and $R^A$–$R^D$ are monovalent hydrocarbon radicals preferably selected from the group consisting of alkyl, alkenyl, aryl, alkaryl, aralkyl, and cycloalkyl moieties or radicals, optionally substituted with suitable heteroatom-containing functional groups. The onium salts are generally selected to be less preferentially less soluble in the less polar of the two distinct liquid phases. Any of the salts disclosed in the U.S. Pat. No. 3,992,432 will be found effective, but most preferred are those in which the total number of carbon atoms in $R^A, R^B, R^C$, and $R^D$ cumulatively range from about 13 to about 57, and preferably range from about 16 to about 30. Most preferred onium salts have Y=N, and hydrocarbon radicals where $R^A$ is $CH_3$, and $R^B$, $R^C$, and $R^D$ are each selected from the group consisting of n-$C_2H_5$, n-$C_4H_5$; n-$C_5H_{11}$; mixed $C_5H_{17}$; n-$C_{12}H_{25}$; n-$C_{18}H_{37}$; mixed $C_8$–$C_{10}$ alkyl; and the like. However, $R^A$ may also be selected from $C_2H_5$n-$C_3H_7$ and n-$C_4H_9$ benzyl.

Various counterions may be used, including $Cl^-$, $Br^-$, $I^-$, $NO_3^-$, $SO_4^{-2}$, $HSO_4^-$ and $CH_2CO_2^-$. Most preferred is $Cl^-$.

The tertiary amines or triamines useful as phase transfer catalysts in this synthesis include the alkyl amines and the aryldialkylamines, exemplified by tributylamine and phenyldibutylamine respectively, which are commonly available, wherein each alkyl may have from 1 to about 16 carbon atoms.

The polyethers useful as catalysts in this synthesis include cyclic polyethers such as the crown ethers, disclosed in *Agenwandte Chemie*, supra, and acyclic polyethers having the formula $$R—O—R^E$$

wherein R and $R^E$ are, independently, alkyls having from 1 to about 16 carbon atoms, or alkyl containing substituted functional groups such as hydroxy, sulfur, amine, ether, etc. Most preferred acyclic polyethers have the formula $$R—(OCH_2CH_2)_r OR''$$

wherein
R is an alkyl having from 1 to about 16 carbon atoms
R'' is an alkyl having from 1 to about 16 carbon atoms, or H, and
r is an integer in the range from 0 to about 300.

Most preferred are commonly available polyethers such as: tetraethylene glycol dimethyl ether; polyethylene oxide (mol wt. About 5000); poly(ethylene glycol methyl ether); 1,2-dimethoxyethane; diethyl ether, and the like.

Polyether catalysts are especially desirable in this ketoform synthesis because they are directive so as to produce a preponderance of the desired symmetrically substituted isomer, in a reaction which is remarkably free of undesirable byproducts, which reaction proceeds with a relatively mild exotherm so that the reaction is controllable.

The organic solvent may be any solvent in which the reactants are soluble and include hydrohalomethylenes, particularly hydrochloromethylenes, sulfolane, dibutyl ether, dimethyl sulfone, diisopropyl ether, di-n-propyl ether, 1,4-dioxane, tetrahydrofuran, benzene, toluene, hexane, carbon tetrachloride, heptane, mineral spirits and the like. Most preferred solvents are heptanes and mineral spirits. Solvent is generally utilized in an amount generally from about 10 to about 500 percent and preferably from about 50 percent to about 200 percent based on the total weight of the reactants.

Insofar as the reactive components are concerned, any of various ketones having the general formula:

$$R^1—\overset{\overset{O}{\|}}{C}—R^2$$

can be employed in the synthesis, wherein $R^1$ and $R^2$ are described herein above. As carbon disulfide is the controlling agent in the reaction, the ketone is generally used in an amount from about 110 mole percent to about 2,000 mole percent per mole of carbon disulfide. When the ketone is used as a solvent, it is generally utilized in an amount of from about 150 mole percent to about 300 mole percent, and preferably from about 180 mole percent to about 250 mole percent per mole of carbon disulfide.

The alkali bases suitable for use in the synthesis of the present invention include, but are not limited to, sodium hydroxide and potassium hydroxide. The base is utilized in an amount generally from about 5 times to about 15 times the number of moles of carbon disulfide and preferably from about 6 to about 10 times the number of moles of carbon disulfide utilized in the reaction.

The acids used in the acidification step include, but are not limited to, hydrochloric acid, sulfuric acid, phosphoric acid, etc. The acids are utilized in amounts suitable to make the aqueous solution acidic.

The haloform of the present invention has the general formula $CHX_3$ wherein X is, independently, chlorine or bromine. The amount of haloform used in the present invention is generally from about 110 mole percent to about 2000 mole percent, desirably from about 150 mole percent to about 300 mole percent, and preferably 180 mole percent to about 250 mole percent per mole of carbon disulfide. Examples of haloforms include, but are not limited to, chloroform and bromoform, and chloroform is the preferred haloform of the present invention.

Alternatively, instead of adding both a haloform and a ketone, to the reaction mixture, an α-trihalomethyl-α-alkanol can be substituted therefore. The amount of α-trihalomethyl-α-alkanol utilized in the reaction generally is from about 110 mole percent to about 2000 mole percent, desirably is from about 150 mole percent to about 300 mole percent, and preferably is from about 180 mole percent to about 250 mole percent per mole of carbon disulfide. The general formula of the α-trihalomethyl-α-alkanol is generally represented as follows:

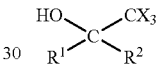

wherein X, $R^1$ and $R^2$ are defined above.

While not wishing to be limited to any particular mechanism, it is believed that the specific mechanism for the reaction process is as follows:

Initially, the carbon disulfide and sodium hydroxide are reacted.

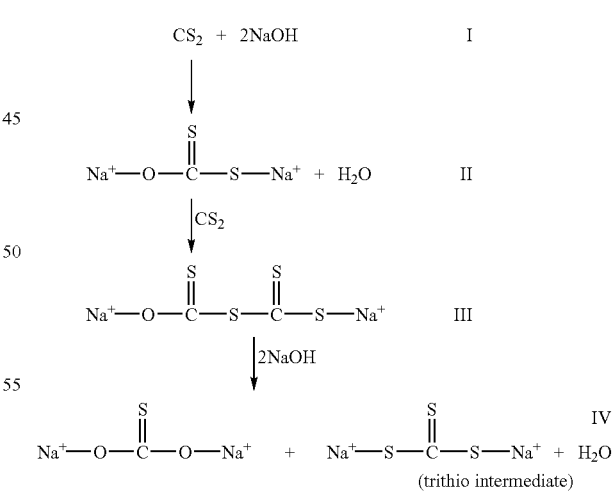

In the subsequent step of the reaction, the chloroform is reacted with the ketone as follows:

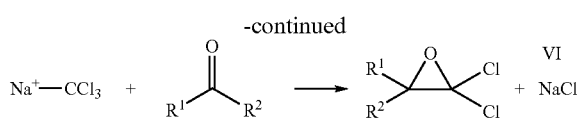

-continued (1-disubstituted-2-dichloroepoxide)

Then, the following is reacted:

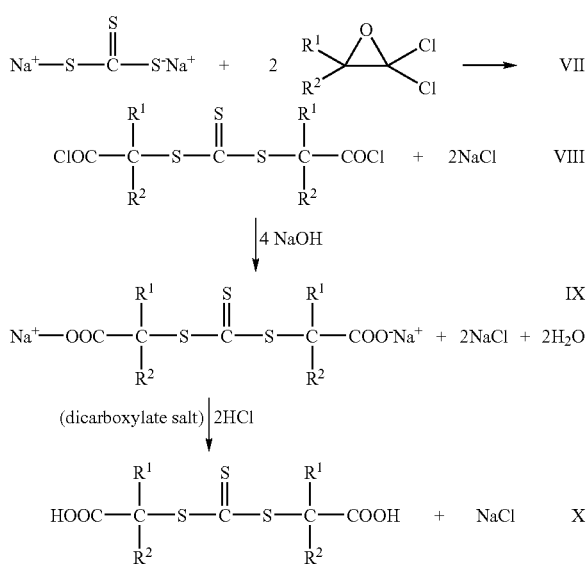

The overall reaction is as follows:

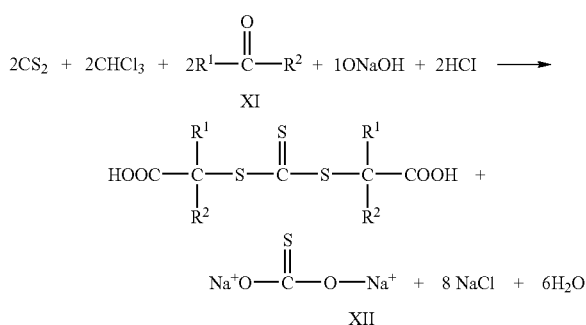

The s,s'-bis-(α,α'-disubstituted-α"-acetic acid)-trithiocarbonate compounds produced by the present invention can generally be classified as inifertors, meaning that they act as both a chain transfer agent and an initiator. The use of other types of inifertors for block copolymers was discussed by Yagei and Schnabel in *Progress in Polymer Science* 15, 551 (1990) and is hereby fully incorporated by reference.

Thus, the compounds of the present invention can be utilized as initiators to initiate or start the polymerization of a monomer. They can also act as a chain transfer agent, which interrupts and terminates the growth of a polymer chain by formation of a new radical which can act as a nucleus for forming a new polymer chain. The compounds can also be utilized as terminators in that when most of initiating radicals and monomers are consumed, the compounds are incorporated in the polymers as a dormant species. Desirably though, another compound, such as those listed herein below, is often used as an initiator in the free radical polymerization process as described herein below, and the s,s'-bis-(α,α'-disubstituted-α"-acetic acid)-trithiocarbonate compounds of the present invention will act as a chain-transfer agent.

The s,s'-bis-(α,α'-disubstituted-α"-acetic acid) trithiocarbonate compounds of the present invention can be used as chain transfer agents in a free radical polymerization process to provide polymerizations which have living characteristics and polymers of controlled molecular weight and low polydispersity, as well as for forming telechelic polymers.

A living polymerization is a chain polymerization which proceeds in the absence of termination and chain transfer. The following experimental criteria can be utilized to diagnose a living polymerization.

1. Polymerization proceeds until all monomer has been consumed. Further addition of monomer results in continued polymerization.
2. The number average molecular weight, $M_n$, (or $X_n$, the number average degree of polymerization), is a linear function of conversion.
3. The number of polymer molecules (and active centres) is constant and independent of conversion.
4. The molecular weight can be controlled by the stoichiometry of the reaction.
5. Narrow molecular weight distribution polymers are produced.
6. Chain-end functionalized polymers can be prepared in quantitative yields.
7. In radical polymerization, the number of active end groups should be 2, one for each end.

Besides those mentioned above, other criteria can also help to determine the living character of polymerization. For radical living polymerization, one is the ability of the polymer isolated from the first step of polymerization to be used as a macroinitiator for the second step of a polymerization in which block copolymers or grafted polymers are ultimately formed. To confirm the formation of block copolymers, measurements of molecular weights and a determination of the structure of the blocks are employed. For structure measurements, the examination of NMR or IR signals for the segments where individual blocks are linked together and a determination of the end groups are both very important. In radical polymerization, only some of the criteria for living polymerizations are actually fulfilled. Due to their ability to undergo further polymerization, these types of polymers can also be called 'reactive polymers'. A more detailed description of living polymerization can be found in "Living Free-Radical Block Copolymerization Using Thio-Inifertors", by Anton Sebenik, *Progress in Polymer Science*, vol. 23, p. 876, 1998.

The living polymerization processes can be used to produce polymers of narrow molecular weight distribution containing one or more monomers sequences whose length and composition are controlled by the stoichiometry of the reaction and degree of conversion. Homopolymers, random copolymers or block polymers can be produced with a high degree of control and with low polydispersity. Low polydispersity polymers are those with polydispersities that are significantly less than those produced by conventional free radical polymerization. In conventional free radical polymerization, polydispersities (polydispersity is defined as the ratio of the weight average to the number average molecular weight $M_w/M_n$) of the polymers formed are typically greater than 2.0. Polydispersities obtained by utilizing the s,s'-bis-(α,α'-disubstituted-α"-acetic acid)-trithiocarbonate compounds and derivatives thereof of the present invention are preferably 1.75 or 1.5, or less, often 1.3 or less, and, with appropriate choice of the chain transfer agent and the reaction conditions, can be 1.25 or less.

When the s,s'-bis-(α,α'-disubstituted-α"-acetic acid)-trithiocarbonates compounds are utilized only as chain-transfer agents, the polymerization can be initiated with other initiators at lower temperature while yielding polymers with similarly controlled fashion.

Free radical polymerizations utilizing the s,s'-bis-(αα'-disubstituted-α"-acetic acid)-trithiocarbonate compounds as both initiators and chain transfer agents generally form telechelic polymers. When an initiator other than the s,s'-bis-(α,α'-disubstituted-α"-acetic acid)-trithiocarbonate compound is also utilized, a polymer having a single functional end group is formed in proportion to the amount of said other initiator to this s,s'-bis-(α,α'-disubstituted-α"-acetic acid)-trithiocarbonate compound utilized.

The free radical living polymerization process of the invention can be applied to any monomers or monomer combinations which can be free-radically polymerized. Such monomers include one or more conjugated diene monomers or one or more and vinyl containing monomers, or combinations thereof.

The diene monomers have a total of from 4 to 12 carbon atoms and examples include, but are not limited to, 1,3-butadine, isoprene, 1,3-pentadiene, 2,3-dimethyl-1-3-butadeine, 2-methyl-1,3-pentadiene, 2,3-dimethyl-1,3-pentadiene, 2-phenyl-1,3-butadiene, and 4,5-diethyl-1,3-octadiene, and combinations thereof.

The vinyl containing monomers have the following structure:

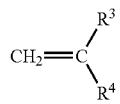

where $R^3$ comprises hydrogen, halogen, $C_1$ to $C_4$ alkyl, or substituted $C_1$–$C_4$ alkyl wherein the substituents, independently, comprise one or more hydroxy, alkoxy, aryloxy ($OR^5$), carboxy, acyloxy, aroyloxy($O_2CR^5$), alkoxy-carbonyl($CO_2R^5$), or aryloxy-carbonyl; and $R^4$ comprises hydrogen, $R^5$, $CO_2H$, $CO_2R^5$, $COR^5$, $CN$, $CONH_2$, $CONHR^5$, $O_2CR^5$, $OR^5$, or halogen. $R^5$ comprises $C_1$ to $C_{18}$ alkyl, substituted $C_1$–$C_{18}$ alkyl, $C_2$–$C_{18}$ alkenyl, aryl, heterocyclyl, aralkyl, or alkaryl, wherein the substituents independently comprise one or more epoxy, hydroxy, alkoxy, acyl, acyloxy, carboxy, (and salts), sulfonic acid (and salts), alkoxy- or aryloxy-carbonyl, sicyanato, cyano, silyl, halo and dialkylamino. Optionally, the monomers comprise maleic anhydride, N-vinyl pyrrolidone, N-alkylmaleimide, N-arylmaleimide, dialkyl fumarate and cyclopolymerizable monomers. Monomers $CH_2=CR^3R^4$ as used herein include $C_1$–$C_8$ acrylates and methacrylates, acrylate and methacrylate esters, acrylic and methacrylic acid, styrene, α methyl styrene, $C_1$–$C_{12}$ alkyl styrenes with substitute groups both either on the chain or on the ring, acrylamide, methacrylamide, and methacrylonitrile, mixtures of these monomers, and mixtures of these monomers with other monomers. As one skilled in the art would recognize, the choice of comonomers is determined by their steric and electronic properties. The factors which determine copolymerizability of various monomers are well documented in the art. For example, see: Greenley, R. Z., in *Polymer Handbook, 3rd Edition* (Brandup, J., and Immergut, E. H. Eds.) Wiley: New York, 1989 p11/53.

Specific monomers or comonomers include the following: methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene. methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile. styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-terbtbutylmethacrylamide, N-n-butylmethacrylamide, N-methylolmethacrylamide, N-ethylotmethacrylamide. N-tert-butylacrylamide. N-n-butylacrylamide, N-methylolacrylamide, N-ethylolacrylamide, vinyl benzoic acid (all isomers), dethylaminostyrene (all isomers), alpha-methylvinyl benzoic acid (all isomers), dethylamino alpha-methylstyrene (all isomers). p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylslylpropyl methacrylate, dibutoxymethylsilypropyl methacrylate, diisopropoxymethylsilylpropyl methacrylate, dimethoxysilylpropyl methacrylate, diethoxysilylpropyl methacrylate, dibutoxy, silylpropyl methacrylate, diisopropoxysilylpropyl methacrylate, trimethoxysilylpropyl acrylate, triethoxysifylylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl amiate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene, and propylene, and combinations thereof.

Preferred monomers are $C_1$–$C_8$ acrylates, $C_1$–$C_8$ methacrylates, styrene, butadiene, isoprene and acrylonitrile.

As noted above, in order to initiate the free radical polymerization process, it is often desirable to utilize an initiator as a source for initiating free radicals. Generally, the source of initiating radicals can be any suitable method of generating free radicals such as the thermally induced homolytic scission of a suitable compound(s) (thermal initiators such as peroxides, peroxyesters, or azo compounds), the spontaneous generation from monomer (e.g., styrene), redox initiating systems, photochemical initiating systems or high energy radiation such as electron beam, X- or gamma-radiation. The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture. The s,s'-bis-(α,α'-disubstituted-α"-acetic acid)-trithiocarbonate compounds of the invention can serve as an initiator, but the reaction must be run at a higher temperature. Therefore, optionally it is desirable to utilize an initiator other than the s,s'-bis-(α, α'-disubstituted-α"-acetic acid)-trithiocarbonates compounds of the present invention.

Thermal initiators are chosen to have an appropriate half-life at the temperature of polymerization. These initiators can include one or more of the following compounds: 2,2'-azobis(isobutyronitrile)(AIBN), 2,2'-azobis(2-cyano-2-butane), dimethyl 2,2'-azobisdimethylisobutyrate, 4,4'-azobis(4-cyanopentanoic acid), 1,1'-azobis(cyclohexanecarbanitrile), 2-(t-butylazo)-2-cyanopropane, 2,2'-azobis[2-methyl-N-(1,1)-bis(hydoxymethyl)-2-hydroxyethyl] propionamide, 2,2'-azobis[2-methyl-N-hydroxyethyl)]-propionamide, 2,2'-azobis(N,N'-dimethyleneisobutyramidine) dihydrochloride, 2,2'-azobis(2-amidinopropane) dihydrochloride, 2,2'-azobis(N,N'-dimethyleneisobutyramine), 2,2'-azobis(2-methyl-N-[1,1-bis(hydroxymethyl)-2-hydroxyethyl] propionamide), 2,2'-azobis(2-methyl-N-[1,1-bis (hydroxymethyl) ethyl] propionamide), 2,2'-azobis[2-methyl-N-(2-hydroxyethyl) propionamide], 2,2'-azobis (isobutyramide) dehydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butylperoxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroylperoxide, potassium peroxydisulfate, ammonium peroxydisulfate, di-t-butyl hyponitrite, dicumyl hyponitrite.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems production under the conditions of the polymerization; these initiating systems can include combinations of the following oxidants and reductants:

oxidants: potassium peroxydisulfate, hydrogen peroxide, t-butyl hydroperoxide reductants: iron (11), titanium (111), potassium thiosulfite, potassium bisulfite.

Other suitable initiating systems are described in recent texts. See, for example, Moad and Solomon "The Chemistry of Free Radical Polymerization". Pergamon, London. 1995. pp 53–95.

The preferred initiators of the present invention are 2,2'-azobis(isobutyronitrile)(AIBN), or 4,4'-azobis(4-cyanopentanoic acid), or 2,2'-azobis(2-cyano-2-butane), or 1,1'-azobis (cyclohexanecarbanitrile). The amount of initiators utilized in the polymerization process can vary widely as generally from about 0.001 percent to about 99 percent, and desirably from about 0.01 percent to about 50 or 75 percent based on the total moles of chain transfer agent utilized. Preferably small amounts are utilized from about 0.1 percent to about 5, 10, 15, 20, or 25 mole percent based on the total moles of chain transfer agent utilized, i.e. said s,s'-bis-(α,α'-disubstituted-α"-acetic acid)-trithiocarbonate compounds. In order to form polymers which are predominately telechelic, initiators other than the s,s'-bis-(α,α'-disubstituted-α"-acetic acid)-trithiocarbonate compounds are utilized in lesser amounts, such as from about 0.001 percent to about 5 percent, desirably from about 0.01 percent to about 4.5 percent, and preferably from about 0.1 percent to about 3 percent based on the molar equivalent to the total moles of chain transfer agent utilized.

Optionally, as noted above, solvents may be utilized in the free radical polymerization process. Examples of such solvents include, but are not limited to, $C_6$–$C_{12}$ alkanes, toluene, chlorobenzene, acetone, t-butyl alcohol, and dimethylformamide. The solvents are chosen so that they do not chain transfer themselves. The amount of solvent utilized in the present invention polymerization process is generally from about 10 percent to about 500 percent the weight of the monomer, and preferably from about 50 percent to about 200 percent the weight of the monomer utilized in the polymerization.

As stated above, it is preferable to utilize the s,s'-bis-(α, α'-disubstituted-α"-acetic acid)-trithiocarbonate compounds of the invention as chain transfer agents in the free radical polymerization process. The amount of chain transfer agent (CTA) utilized depends on the desired molecular weight of the polymer to be formed and can be calculated as known by one skilled in the art. A formula for calculating the amount of chain transfer agent is as follows:

$$Mn \text{ of polymer} = \left( \frac{\text{weight of monomer} \times \text{molecular weight } CTA}{\text{Weight of } CTA} \right) + \text{molecular weight of } CTA \qquad \text{XII(a)}$$

While not wishing to be limited to any particular mechanism, it is believed that the mechanism of the free radical living polymerization process is as follows when using a vinyl monomer:

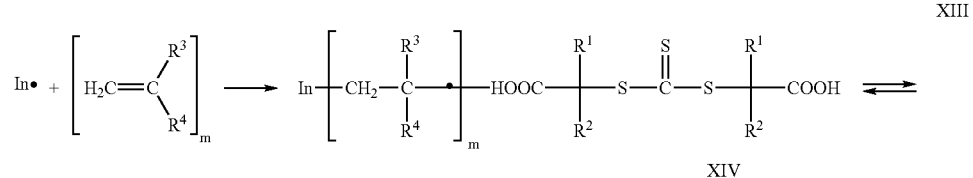

XIII

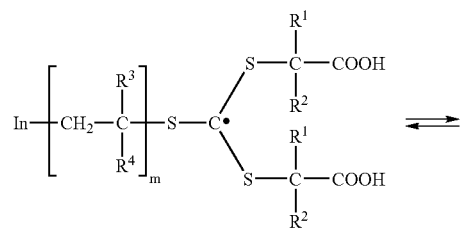

XIV

-continued
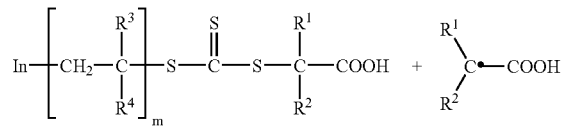
XV
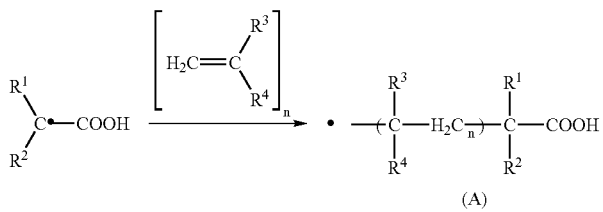
XVI
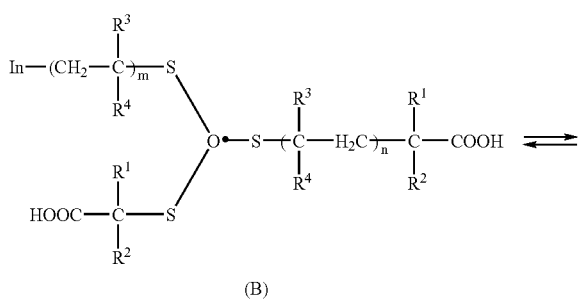
XVII
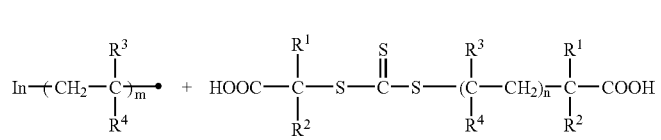
XVIII
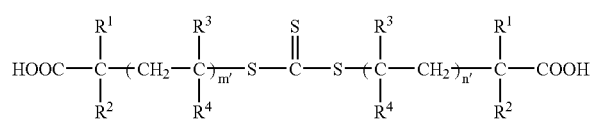
XIX
Alternatively, the reaction can proceed as follows:
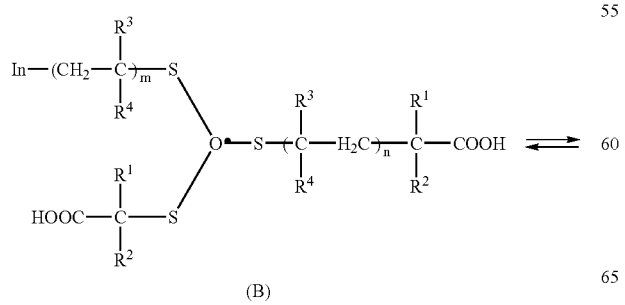
XX
-continued
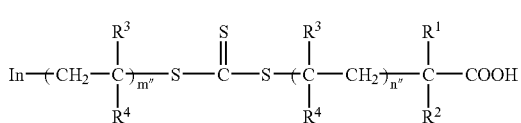
XXI
XXII As can be seen from the above mechanism, polymers having two different structures, see XIX and XXII, can be formed. The resulting polymers are either telechelic polymers (formed by the trithiocarbonate compounds of the present invention) with identical functional groups at the ends of the chain, or a polymer having a single functional end group and also an initiator terminated chain (formed by using a conventional initiator such as AIBN). As stated above, the ratios between the resulting polymers can be controlled to give desired results and generally depends on the amount of initiator utilized. Obviously, if the initiator is the only s,s'-bis-(α,α'-disubstituted-α"-acetic acid)-trithiocarbonate compound of the present invention, the resulting polymers are always telechelic. The greater the amount of the other initiator utilized, proportionally decreases the amount of telechelic polymers formed. Generally, the amount of the repeat group m, m', m", n, n', or n", is generally from about 1 to about 10,000, desirably from about 5 to about 500, and preferably from about 10 to about 200. Inasmuch as one or more vinyl monomers and/or one or more diene monomers can be utilized, it is to be understood that repeat groups of the polymers of the present invention are generally indicated by formulas XIX and XXII and can be the same or different. That is, random copolymers, terpolymers, etc., can be formed within either of the two repeat groups noted, as well as block copolymers which can be formed by initially adding one monomer and then subsequently adding a different monomer (e.g. an internal block copolymer).

The polymers formed by the present invention can be generally represented by the following formula:

mers for example. Therefore, any of the above listed monomers, i.e. conjugated dienes or vinyl containing monomers, can be utilized to form block copolymers utilizing the s,s'-bis-(α,α'-distributed-α"-acetic acid)-trithiocarbonate compounds as chain transfer agent. Alternatively, the substituents may be non-reactive such as alkoxy, alkyl, or aryl. Reactive groups should be chosen such that there is no adverse reaction with the chain transfer agents under the conditions of the experiment.

The process of this invention can be carried out in emulsion, solution or suspension in either a batch, semi-batch, continuous, or feed mode. Otherwise-conventional procedures can be used to produce narrow polydispersity polymers. For lowest polydispersity polymers, the chain transfer agent is added before polymerization is commenced. For example, when carried out in batch mode in solution, the reactor is typically charged with chain transfer agent and monomer or medium plus monomer. The desired amount of initiator is then added to the mixture and the mixture is heated for a time which is dictated by the desired conversion and molecular weight. Polymers with broad, yet controlled, polydispersity or with multimodal molecular weight distribution can be produced by controlled addition of the chain transfer agent over the course of the polymerization process.

In the case of emulsion or suspension polymerization the medium will often be predominately water and the conventional stabilizers, dispersants and other additives can be present. For solution polymerization, the reaction medium can be chosen from a wide range of media to suit the monomer(s) being used.

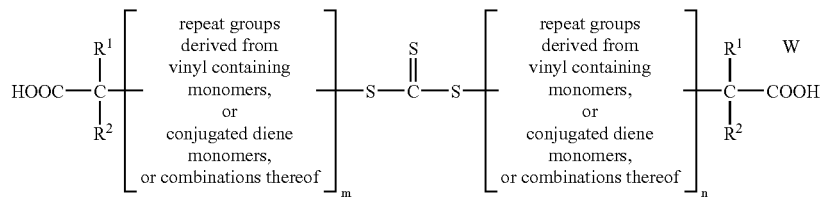

wherein such monomers are described herein above. Of course, the above formula can contain an initiator end group thereon as in XXII.

The reaction conditions are chosen as known to one skilled in the art so that the temperature utilized will generate a radical in a controlled fashion, wherein the temperature is generally from about room temperature to about 200° C. The reaction can be run at temperatures lower than room temperature, but it is impractical to do so. The temperature often depends on the initiator chosen for the reaction, for example, when AIBN is utilized, the temperature generally is from about 40° C. to about 80° C., when azo dicyanodivaleric acid is utilized, the temperature generally is from about 50° C. to about 90° C., when di-t-butylperoxide is utilized, the temperature generally is from about 110° C. to about 160° C., when s,s'-bis-(α, α'-disubstituted-α"-acetic acid) is utilized, the temperature is generally from about 80° C. to about 200° C.

The low polydispersity polymers prepared as stated above by the free radical polymerization can contain reactive end groups from the monomers which are able to undergo further chemical transformation or reaction such as being joined with another polymer chain, such as to form block copoly- As already stated, the use of feed polymerization conditions allows the use of chain transfer agents with lower transfer constants and allows the synthesis of block polymers that are not readily achieved using batch polymerization processes. If the polymerization is carried out as a feed system the reaction can be carried out as follows. The reactor is charged with the chosen medium, the chain transfer agent and optionally a portion of the monomer(s). The remaining monomer(s) is placed into a separate vessel. Initiator is dissolved or suspended in the reaction medium in another separate vessel. The medium in the reactor is heated and stirred while the monomer+medium and initiator+medium are introduced over time, for example by a syringe pump or other pumping device. The rate and duration of feed is determined largely by the quantity of solution the desired monomer/chain transfer agent/initiator ratio and the rate of the polymerization. When the feed is complete, heating can be continued for an additional period.

Following completion of the polymerization, the polymer can be isolated by stripping off the medium and unreacted monomer(s) or by precipitation with a non-solvent. Alternatively, the polymer solution/emulsion can be used as such, if appropriate to its application.

The invention has wide applicability in the field of free radical polymerization and can be used to produce polymers and compositions for coatings, including clear coats and base coat finishes for paints for automobiles and other vehicles or industrial, architectural or maintenance finishes for a wide variety of substrates. Such coatings can further include pigments, durability agents, corrosion and oxidation inhibitors, rheology control agents, metallic flakes and other additives. Block and star, and branched polymers can be used as compatibilizers, thermoplastic elastomers, dispersing agents or rheology control agents. Additional applications for polymers of the invention are in the fields of imaging, electronics (e.g., photoresists), engineering plastics, adhesives, sealants, paper coatings and treatments, textile coatings and treatments, inks and overprint varnishes, and polymers in general.

As can be seen in the above shown polymerization mechanism, the s,s'-bis-($\alpha$,$\alpha$'-disubstituted-$\alpha$"-acetic acid)-trithiocarbonate compound can be utilized to create telechelic polymers having two functional groups at both chain ends.

The term "telechelic polymer" was proposed in 1960 by Uraneck et al. to designate relatively low molecular weight macromolecules possessing one or more, and preferably two reactive functional groups, situated at the chain ends, thereof. The functional end groups of both the s,s'-bis-($\alpha$,$\alpha$'-disubstituted-$\alpha$"-acetic acid)-trithiocarbonate compound and the polymers formed therefrom, have the capacity for selective reaction to form bonds with another molecule. The functionality of a telechelic polymer or prepolymer is equal to the number of such end groups. Telechelic polymers containing a functional group, such as COOH, at each end are useful for synthesizing further chain extended copolymers and block copolymers.

The interest in telechelic polymers resides in the fact that such polymers can be used, generally together with suitable linking agents, to carry out three important operations: (1) chain extension of short chains to long ones by means of bifunctional linking agents, (2) formation of networks by use of multifunctional linking agents, and (3) formation of (poly)block copolymers by combination of telechelics with different backbones. These concepts are of great industrial importance since they form the basis of the so-called "liquid polymer" technology exemplified by the "reaction injection molding" (RIM). Great interest has also been shown by the rubber industry because the formation of a rubber is based on network formation. In classical rubber technology, this is achieved by the cross-linking of long chains that show high viscosity. The classical rubber technology, therefore, requires an energy-intensive mixing operation. The use of liquid precursors, which can be end-linked to the desired network, offers not only processing advantages, but in some cases, also better properties of the end-product. Further information about telechelic polymers and synthesis thereof can be found in "Telechelic Polymers: Synthesis and Applications" by Eric J. Goethe, CRC Press, Boca Raton, Fla., 1989.

The reaction conditions for the reactive functional acid end groups of the telechelic polymers or s,s'-bis-($\alpha$,$\alpha$'-disubstituted-$\alpha$"-acetic acid)-trithiocarbonate compounds of the present invention are generally the same as those for forming the above noted free radical polymers. The acid in the monomeric or in the polymeric form can be transformed to its derivatives in the conventional manner. For example, the ester can be made by refluxing the acid in alcohol with an acid catalyst with removal of water. Amides can be formed by heating the acid with an amine with the removal of water. 2-hydroxy-ethyl ester can be formed by directly reacting the acid with an epoxide with or without a catalyst such as triphenylphosphine or an acid like toluene-sulfonic acid. As seen by the examples below, any of the above noted monomers such as the one or more diene monomers or one or more vinyl containing monomers, can be utilized to form the telechelic monomers from the bis-($\alpha$,$\alpha$'-distributed-$\alpha$"-acetic acid)-trithiocarbonate compounds of the present invention. Any of the above noted components, such as solvent, etc., can be utilized in the herein above stated amounts.

The acid groups of the s,s'-bis-($\alpha$,$\alpha$'-disubstituted-$\alpha$"-acetic acid)-trithiocarbonate compound can be converted to other functional groups either before or after polymerization. Even if the s,s'-bis-($\alpha$,$\alpha$'-disubstituted-$\alpha$"-acetic acid)-trithiocarbonate compounds have functional end groups which have been converted from the acid end groups before polymerization, the monomers added during polymerization still add to the chain between the sulfur-tertiary carbon as shown in the mechanisms above as well as below at XXIII and XXIV. The carboxylic end groups of the s,s'-bis-($\alpha$,$\alpha$'-disubstituted-$\alpha$"-acetic acid)-trithiocarbonate compounds or the polymerized s,s'-bis-($\alpha$,$\alpha$'-disubstituted-$\alpha$"-acetic acid)-trithiocarbonate compounds can be converted or changed into other functional end groups such as esters, thioesters, amides, beta mercapto esters, beta hydroxy esters, or beta amino esters. Examples of these functional end groups are shown below.

An example reaction forming a telechelic polymer from the s,s'-bis-($\alpha$,$\alpha$'-disubstituted-$\alpha$"-acetic acid)-trithiocarbonate compounds of the invention when using a vinyl monomer is as follows:

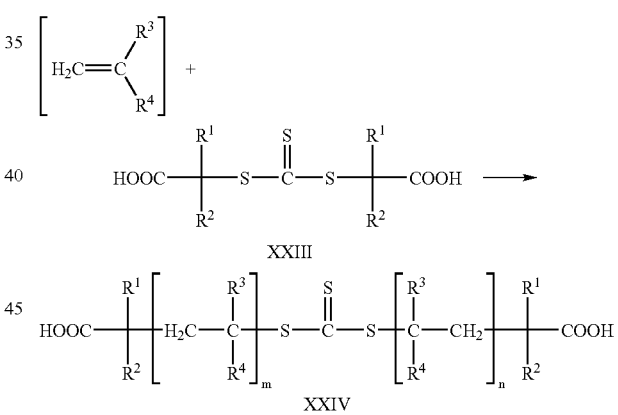

Of course, it is to be understood as indicated above, that the repeat units m and n can be derived either from conjugated diene monomers, or the indicated vinyl monomers, or combinations thereof, as generally set forth in formula W.

Subsequently, other functional end groups can be derived from the acid groups of the s,s'-bis-($\alpha$,$\alpha$'-disubstituted-$\alpha$"-acetic acid)-trithiocarbonate compound and can generally be represented by the formula:

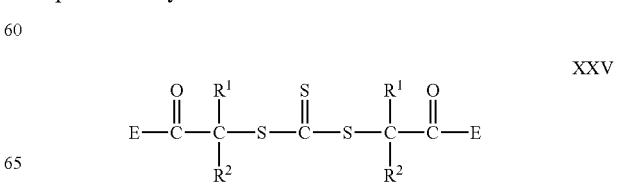

where E is set forth below. For example,

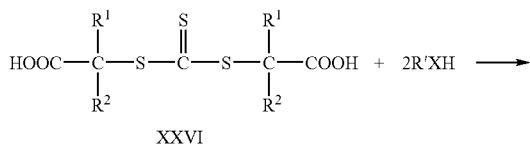

XXVI

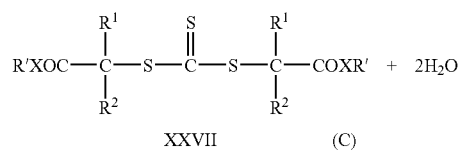

XXVII (C)

wherein E is XR', that is R', independently, comprises H, $C_1$–$C_{18}$ alkyls which can be optionally substituted with one or more halogen, hydroxyl, or alkoxy, $C_1$–$C_{18}$ hydroxyalkyls, and $C_1$–$C_{18}$ aminoalkyls and X comprises oxygen, sulfur, NH, or NR'.

The following is still another example of functional end groups which can be derived from the acid:

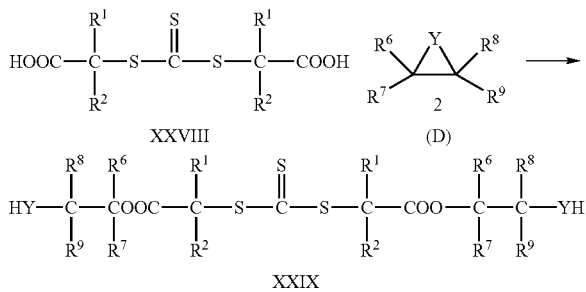

XXVIII (D)

XXIX wherein E is

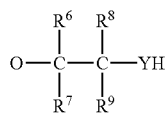

XXX that is where $R^6$ through $R^9$, independently comprise H, $C_1$–$C_{18}$ alkyls, aryl groups or substituted aryl groups having from 1 to 6 substituents on the ring, such as halogen, hydroxyl, or alkoxy, $C_1$–$C_{18}$ hydroxyalkys, $C_1$–$C_{18}$ aminoalkyls, $C_1$–$C_{18}$ mercapto alkyls, and the like. Y can comprise oxygen, sulfur, NH, or $NR^6$ to $R^9$.

A further example of still other functional end groups which can be derived from the acid groups of the s,s'-bis-(α,α'-disubstituted-α"-acetic acid)-trithiocarbonate compounds is as follows:

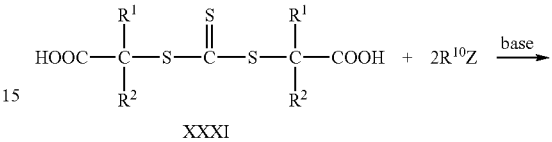

XXXI

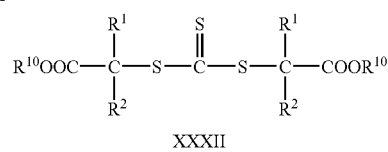

XXXII wherein E is $OR^{10}$, that is where Z can comprise a leaving group, such as a halide or alkylsulfonate or aryl sulfonate. $R^{10}$ can comprise $C_1$–$C_{18}$, a alkyl or substituted alkyl wherein said substituent is halogen, hydroxyl, or alkoxy, $C_1$–$C_{18}$ hydroxyalkyl or $C_1$–$C_{18}$ amino alkyl and the like.

Preparation of the above shown methylesters of s,s'-bis-(2-methyl-2-propanoic acid)-trithiocarbonate is as follows: s,s'-bis-(2-methyl-2-propanoic acid) trithiocarbonate ($R^1$, $R^2$=$CH^3$) (2.82 g, 0.01 mole), Sodium carbonate powders (3.18 g, 0.03 mole) and 15 ml dimethyl formamide were stirred under nitrogen at 40° C. while a solution of methyliodide (3.41 g, 0.024 mole) in 2 ml dimethylformamide was added dropwise over 10 minutes. The reaction was stirred at 40–50° C. for 2 hours, poured into 25 ml $H_2O$ and extracted 3 times with a total of 200 ml. ether. The etherate solution was dried over magnesium sulfate and concentrated. The yellow solid was further purified by recrystallization from hexanes. Infrared and H'NMR showed the above desired product.

An example of an already formed telechelic polymer, made from a vinyl monomer, undergoing conversion of the acid end group is as follows:

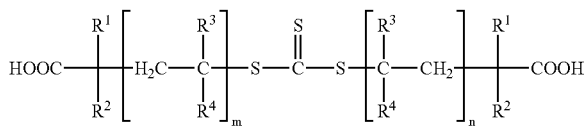

XXXIII

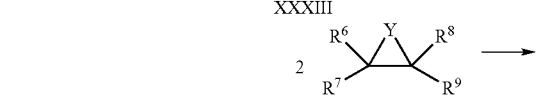

XXXIV where m and n are as set forth above.

The above structure (XXXIV) was formed by reaction of epoxide with s,s'-bis-(2-methyl-2-propanoic acid)-trithiocarbonate (I)($R^1$,$R^2$═$CH_3$, 0.01 mole) of the present invention and Epon® Resin 828 (Resolution Performance Products, reaction product of bisphenol A and epichlorohydrin, 80–85% diglycidyl ethers of bisphenol A) (70 g) and trephenyl phosphine (0.12 g) were heated to 95° C. under nitrogen. The reaction was monitored for the disappearance of the carboxylic acid by titration. It was found the reaction was essentially complete in 1.5 hours. The product structure can be further confirmed by mass spectroscopy.

Another aspect of present invention further relates to forming the following compounds:

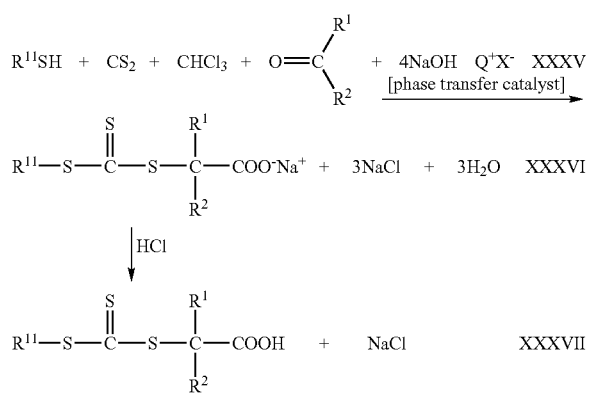

wherein $R^{11}$ comprises a benzyl group, $C_1$–$C_{18}$ alkyl, or substituted alkyl such as halogen, hydroxyl, or alkoxy, $C_1$–$C_{18}$ hydroxyalkyl, carboxylalkyl, or carboalkoxyalkyl. $Q^+X^-$ is a phase transfer catalyst such as tetrabutylammoniumhydrogensulfate, or octadecyltrimethylammoniumchloride (Aliquot 336).

The resulting compound is an s-substituted alkyl-s'-(α,α'-disubstituted-α"-acetic acid)-trithiocarbonate. $R^{11}$ is an alkyl having from 1–18 carbon atoms, aralkyl, hydroxyalkyl, cyanoalkyl, aminoalkyl, carboxylalkyl, or carboalkoxyalkyl, mercaptoalkyl, etc. $R^1$ and $R^2$ are as stated herein above.

When s-substituted alkyl-s'-(α,α'-disubstituted-α"-acetic acid)-trithiocarbonate is employed either as an inifertor, or as a chain-transfer agent, unless $R^{11}$ is carboxyl alkyl, only one end of the polymer has a carboxyl function, i.e. it is no longer a telechelic polymer.

While various polymers have been set forth herein above, it is to be understood that any of the carboxyl terminated polymers, such as W, or the E terminated polymers, and the like, can be reacted with one or more monomers and/or one or more polymers know to the art and to the literature to yield various resulting block polymers which are derived from the same monomer or from two or more different monomers. For example, each acid end group can be reacted with an excess of an epoxy compound such as a glycidyl bisphenol A and then subsequently polymerized with additional glycidyl bisphenol A to form an epoxy polymer. Naturally, other block polymers or copolymers can be reacted with the carboxylic end group or the other end groups generally denoted by E hereinabove.

A further embodiment of the present invention relates to dithiocarbonate compounds which have the general formula:

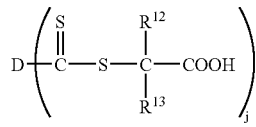

wherein D is ─($OR^{14}$), ─($NR^{15}R^{16}$);

wherein $R^{12}$ and $R^{13}$, independently, can be the same or different, can optionally be substituted, and can be a linear or branched alkyl having from 1 to about 6 or about 12 carbon atoms; or an aryl group having from 6 to about 18 carbon atoms, optionally containing heteroatoms;

The $R^{12}$ and/or $R^{13}$ substituents can, independently, comprise an alkyl having from 1 to 6 carbon atoms; an aryl group; a halogen; a cyano group; an ether having a total of from 2 to about 20 carbon atoms; a nitro; or combinations thereof. $R^{12}$ and $R^{13}$ can also form or be a part of a substituted or unsubstituted cyclic ring having from 3 to about 12 total carbon atoms wherein the substituents are described above. $R^{12}$ and $R^{13}$ are preferably, independently, methyl or phenyl groups;

wherein $R^{14}$ is optionally substituted, and can be a linear or branched alkyl having from 1 to about 12 carbon atoms; an aryl group, optionally saturated or unsaturated; an arylalkyl having from 7 to about 18 carbon atoms; an acyl group; an alkenealkyl having from 3 to about 18 carbon atoms; an alkene group; an alkylene group; an alkoxyalkyl; derived from a polyalkylene glycol; derived from a polyalkylene glycol monoalkyl ether having from 3 to 200 carbon atoms; derived from a polyalkylene glycol monoaryl ether having from 3 to 200 carbon atoms; a polyfluoroalkyl such as 2-trifluoroethyl; a phosphorous containing alkyl; or a substituted or unsubstituted aryl ring containing heteroatoms. Alkyl and alkylene groups from 1 to 6 carbon atoms are preferred;

The $R^{14}$ substituents can comprise an alkyl having from 1 to 6 carbon atoms; an aryl; a halogen such as fluorine or chlorine; a cyano group; an amino group; an alkene group; an alkoxycarbonyl group; an aryloxycarbonyl group; a carboxy group; an acyloxy group; a carbamoyl group; an alkylcarbonyl group; an alkylarylcarbonyl group; an arylcarbonyl group; an arylalkylcarbonyl group; a phthalimido group; a maleimido group; a succinimido group; amidino group; guanidimo group; allyl group; epoxy group; alkoxy group; an alkali metal salt; a cationic substitutent such as a quaternary ammonium salt; a hydroxyl group; an ether having a total of from 2 to about 20 carbon atoms such as methoxy, or hexanoxy; a nitro; sulfur; phosphorous; a carboalkoxy group; a heterocyclic group containing one or more sulfur, oxygen or nitrogen atoms, or combinations thereof;

wherein $R^{15}$ and $R^6$, independently, can be the same or different, optionally can be substituted, optionally can contain heteroatoms; and can be hydrogen; a linear or branched alkyl having from 1 to about 18 carbon atoms, an aryl group having from about 6 to about 18 carbon atoms; an arylalkyl having from about 7 to about 18 carbon atoms; an alkenealkyl having from 3 to about 18 carbon atoms; or derived from a polyalkylene glycol ether having from 3 to about 200 carbon atoms. $R^{15}$ and $R^{16}$ can also be derived from amines such as, but not limited to, piperazine, morpholine, pyrrolidine, piperidine, 4-alkyl amino-2,2,6,6-tetramethyl piperidine, 1-alkylamioalkyl-3,3,5,5-tetramethyl-2-piperazinone, hexamethyleneimine, phenothiazine, iminodibenzyl, phenoxazine, N,N'-diphenyl-1,4-phenylenediamine, dicyclohexylamine and derivatives thereof. $R^{15}$ and $R^{16}$ can also form a substituted or unsubstituted cyclic ring, optionally containing heteroatoms, along with the nitrogen having a total of from 4 to about 12 carbon atoms, such as benzotriazole, tolyltriazole, imidazole, 2-oxazolidone, 4,4-dimethyloxazolidone and the like. The $R^{15}$ and $R^{16}$ substituents, independently, can be the same as described hereabove with respect to $R^{14}$, $R^{15}$ and $R^{16}$ are preferably, independently, a phenyl group or an alkyl or substituted alkyl having from 1 to about 18 carbon atoms such as a methyl group, or $R^{15}$ and $R^{16}$ can be hexamethylene; and wherein j is 1 to about 4, and preferably 1 or 2.

When j of the above formula is greater than 1, the compound formed will be a dimer, trimer, etc. The dithiocarbonate derivative compounds and polymers or copolymers formed from the compounds are thus di-, or tri-, or poly-carboxyl terminated. For example, dicarboxyl terminated compounds of the present invention can be derived from ethylene glycol, 1,3-propanediol, 1,6-hexanediol, 2-methyl-1,3-propanediol, 2,2'-dimethyl-1,3-propanediol, and the like.

It is to be understood throughout the application formulas, reaction schemes, mechanisms, etc., and the specification that metals such as sodium or bases such as sodium hydroxide are referred to and the application of the present invention is not meant to be solely limited thereto. Other metals or bases such as, but not limited to, potassium and potassium hydroxide, respectively, are contemplated by the disclosure of the present invention.

Dithiocarbamates

When D of above formula is $-(NR^{15}R^{16})$, the dithiocarbonate compound is a S-(α,α'-disubstituted-α"-acetic acid) dithiocarbamate having the following formula:

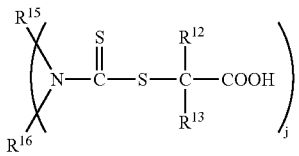

wherein $R^{12}$, $R^{13}$, $R^{15}$, $R^{16}$ and j are as defined hereinabove.

The S-(α,α'-disubstituted-α"-acetic acid) dithiocarbamates are generally a reaction product of a metal salt of a dithiocarbamate, a haloform, and a ketone. A phase transfer catalyst, solvent, and a base such as sodium hydroxide or potassium hydroxide can also be utilized to form the S-(α,α'-disubstituted-α"-acetic acid) dithiocarbamates.

The metal salt of a dithiocarbamate is either prepared or purchased from a supplier such as Aldrich of Milwaukee, Wis. or Acros of Sommerville, N.J. Metal salts of dithiocarbamates can be made in situ from amine, carbon disulfide, and a metal hydroxide as disclosed in the literature. Examples of metal salts of dithiocarbamates include sodium N,N-dimethyl dithiocarbamate and sodium N,N-diethyldithiocarbamate.

The S-(α,α'-disubstituted-α"-acetic acid) dithiocarbamate is formed by combining a metal salt of the dithiocarbamate with a haloform, a ketone, a base, optionally a solvent and a catalyst, in a reaction vessel preferably under an inert atmosphere. The base is preferably added to the other components over a period of time to maintain a preferred temperature range and avoid by-products. The reaction product is subsequently acidified, completing the reaction. The reaction product is isolated as a solid or liquid and is optionally purified.

The limiting agents of the reaction are usually the amine and carbon disulfide, or the metal salt of the dithiocarbamate when utilized. The haloform is utilized in the reaction in an amount from about 0 percent to about 500 percent molar excess, with about 50 percent to about 200 percent molar excess preferred. The ketone is utilized in the reaction in an amount from 0 percent to about 3000 percent molar excess, with about 100 percent to about 1000 percent molar excess preferred. The metal hydroxide when utilized, is present in an amount from 10 percent to 500 percent molar excess, with about 60 percent to 150 percent molar excess preferred.

The abbreviated reaction formula for the S-(α,α'-disubstituted-α"-acetic acid) dithiocarbamate of the present invention is generally as follows:

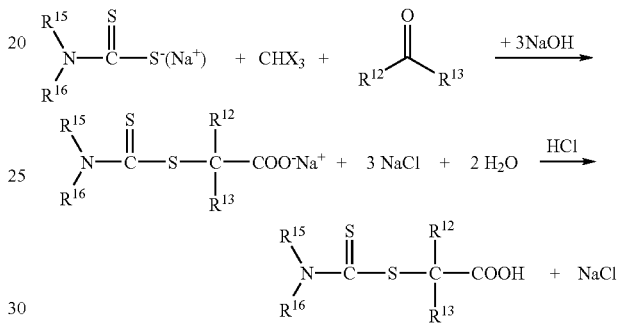

The reaction is carried out at a temperature sufficient to initiate and complete reaction of the reactants in order to produce the S-(α,α'-disubstituted-α"-acetic acid) dithiocarbamate compound in a desired time. The reaction can be carried out at any temperature within a wide range of from about the freezing point of the reaction mass to about the reflux temperature of the solvent. The reaction temperature is generally from about minus 15° C. to about 80° C., desirably from about 0° C. to about 50° C., and preferably from about 15° C. to about 35° C., with about 15° C. to about 25° C. being preferred. The reaction can be performed at atmospheric pressure. The reaction time depends on several factors, with the temperature being most influential. The reaction is generally complete within 20 hours and preferably within about 10 hours.

A catalyst, preferably a phase transfer catalyst, is generally utilized when the optional solvent is used in the reaction. Examples of preferable catalysts and solvents are listed hereinabove and incorporated by reference. Preferred phase transfer catalysts include tricaprylmethylammonium chloride (Aliquot 336), benzyltriethylammonium chloride, and tetrabutylammonium hydrogen sulfate. The amount of catalyst and solvents utilized in the reaction to form the S-(α,α'-disubstituted-α"-acetic acid) dithiocarbamate compound are generally the same as set forth above and herein incorporated by reference. When the ketone is also the solvent, the catalyst is optionally eliminated from the process.

The ketones, haloforms, bases, and acids utilized in the dithiocarbamate reaction can be the same as those listed above for the trithiocarbonate synthesis and amounts thereof are herein incorporated by reference. Alternatively, an α-trihalomethyl-α-alkanol can be utilized in place of the haloform and ketone in the amounts noted hereinabove for the trithiocarbonate synthesis.

It is believed that the reaction scheme for the formation of the S-(α,α'-disubstituted-α"-acetic acid) dithiocarbamate is as follows:

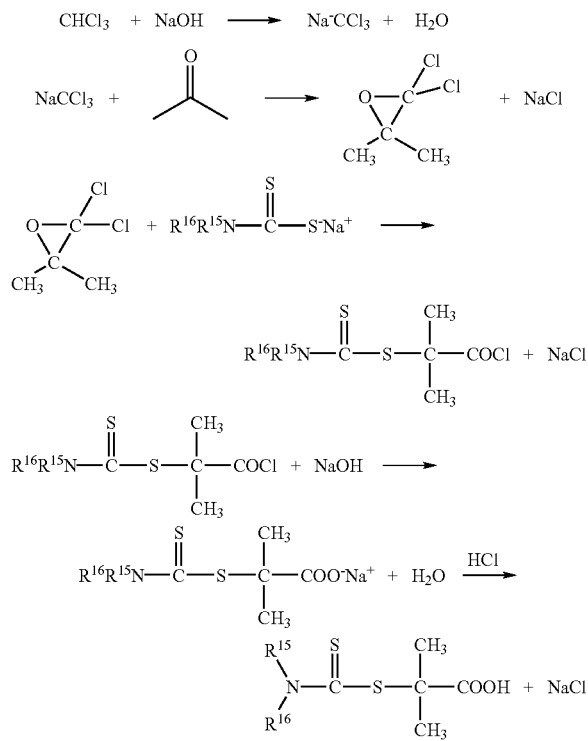

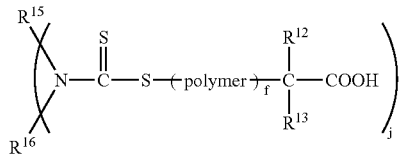

wherein $R^{15}$ and $R^{16}$ are defined hereinabove. A phase transfer catalyst such as tetrabutylammoniumhydrogensulfate or octadecyltrimethylammoniumchloride (Aliquot 336) as mentioned above can be utilized.

The S-($\alpha,\alpha'$-disubstituted-$\alpha''$-acetic acid) dithiocarbamate compounds can be utilized in essentially the same manner as the trithiocarbonate compounds mentioned hereinabove. That is, the S-($\alpha,\alpha'$-disubstituted-$\alpha''$-acetic acid) dithiocarbamate compounds can be utilized as initiators to initiate or start the polymerization of a monomer, as a chain transfer agent which interrupts and terminates the growth of a polymer chain by formation of a new radical which can act as the nucleus for forming a new polymer chain, and/or as a terminator which are incorporated into a polymer as a dormant species. Preferably, the S-($\alpha,\alpha'$-disubstituted-$\alpha''$-acetic acid) dithiocarbamate compounds are utilized as chain transfer agents in free radical polymerizations having living characteristics to provide polymers of controlled molecular weight and low polydispersity.

Dithiocarbamate (Co)Polymers

To this end, the present invention also relates to both a process for forming polymers or copolymer derived from the dithiocarbamate compounds having the following general formula:

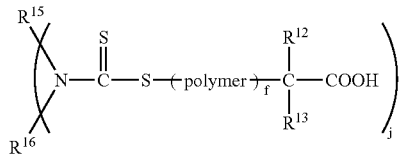

wherein $R^{12}$, $R^{13}$, $R^{15}$, $R^{16}$ and j are defined hereinabove, wherein the polymer is derived from a conjugated diene monomer, or a vinyl containing monomer, or combinations thereof, as defined hereinabove and incorporated by reference, wherein each polymer repeat unit is the same or different, and wherein f is generally from 1 to about 10,000, and preferably from about 3 to about 5,000. Preferred polymers are alkyl acrylate, vinyl acetate, acrylic acid, and styrene. Of course, it is to be understood that when f is 1, the polymer is a single reacted monomer unit.

The above polymers or copolymers can be prepared by bringing into contact with each other the monomer(s) which form(s) the (polymer) repeat units and S-($\alpha,\alpha'$-disubstituted-$\alpha''$-acetic acid)-dithiocarbamate compound, and optionally a) solvent, and b) a radical polymerization initiator; in suitable amounts, as described hereinabove.

It is believed the mechanism is as follows:

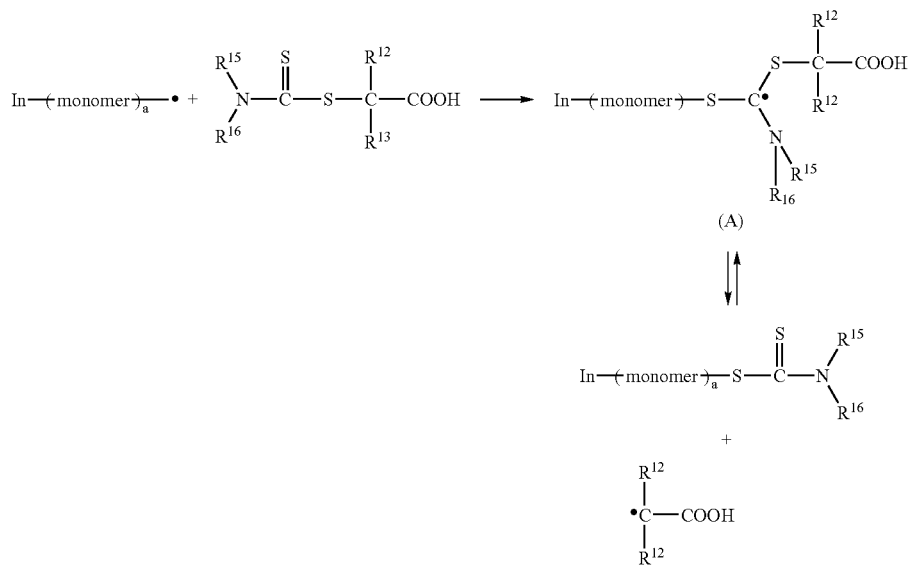

-continued

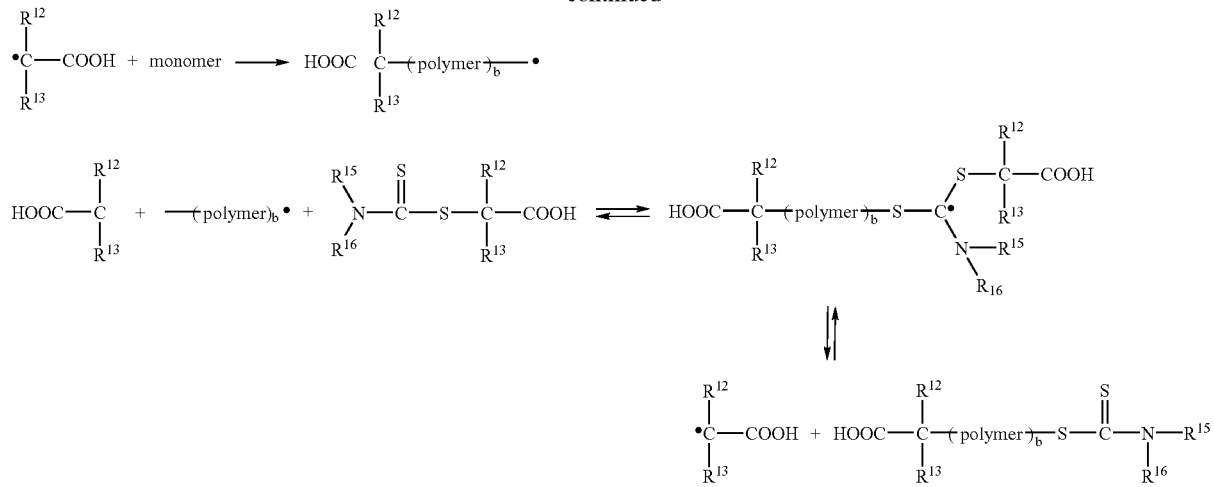

As illustrated by the above reaction formulas, the monomers are polymerized into the dithiocarbamate compounds adjacent to the thiocarbonylthio linkage, between the single bonded sulfur atom and the tertiary carbon atom of the compound.

The dithiocarbamate compounds of the present invention can be used to produce polymers which are substantially colorless. The polymers or copolymers of the dithiocarbamate compounds are hydrolytically stable because the electro-donating amino groups render the thiocarbonyl group less electrophilic and the polymers are also stable toward nucleophiles such as amines.

The reaction conditions are chosen as known to one skilled in the art so that the temperature utilized will generate a radical in a controlled fashion with the temperature being generally from about room temperature to about 200° C. The reaction can be performed at temperatures lower than room temperature, but it is impractical to do so. The temperature often depends on the initiator chosen for the reaction, for example, when AIBN is utilized, the temperature generally is from about 40° C. to about 80° C., when azodicyanodivaleric acid is utilized, the temperature generally is from about 50° C. to about 90° C., when di-t-butylperoxide is utilized, the temperature generally is from about 110° C. to about 160° C., and when S-(α,α'-disubstituted-α"-acetic acid) dithiocarbamate is utilized, the temperature is generally from about 120° C. to about 200° C.

The low polydispersity polymers prepared as stated above by the free radical polymerization can contain reactive end groups from the monomers which are able to undergo further chemical transformation or reaction such as being joined with another polymer chain, such as to form copolymers for example. Therefore, any of the above listed monomers, i.e. conjugated dienes or vinyl containing monomers, can be utilized to form copolymers utilizing the S-(α,α'-disubstituted-α"-acetic acid) dithiocarbamate compounds as chain transfer agent. Moreover, the polymers can be crosslinked using a crosslinker during polymerization. Suitable crosslinkers include, but are not limited to, polyallyl pentaerythritol, polyallyl sucrose, trimethylol propane diacrylate, trimethylol propane triacrylate, glycerol triacrylate, methylene bis-acrylamide and ethylene-glycol diacrylate. Alternatively, the substituents may be non-reactive such as alkoxy, alkyl, or aryl. Reactive groups should be chosen such that there is no adverse reaction with the chain transfer agents under the conditions of the experiment.

The process of this invention can be carried out in emulsion, solution or suspension in either a batch, semi-batch, continuous, or feed mode. Bulk polymerization (no solvent) can also be achieved because propagation is slower. Otherwise-conventional procedures can be used to produce narrow polydispersity polymers. For lowest polydispersity polymers, the chain transfer agent is added before polymerization is commenced. The polydispersity of polymers or copolymers produced from the dithiocarbamates is generally less than about 3.0. For example, when carried out in batch mode in solution, the reactor is typically charged with chain transfer agent and monomer or medium plus monomer. The desired amount of initiator is then added to the mixture and the mixture is heated for a time which is dictated by the desired conversion and molecular weight. Polymers with broad, yet controlled, polydispersity or with multimodal molecular weight distribution can be produced by controlled addition of the chain transfer agent over the course of the polymerization process.

In the case of emulsion or suspension polymerization the medium will often be predominately water and the conventional stabilizers, dispersants and other additives can be present. For solution polymerization, the reaction medium can be chosen from a wide range of media to suit the monomer(s) being used.

As already stated, the use of feed polymerization conditions allows the use of chain transfer agents with lower transfer constants and allows the synthesis of block polymers that are not readily achieved using batch polymerization processes. If the polymerization is carried out as a feed system the reaction can be carried out as follows. The reactor is charged with the chosen medium, the chain transfer agent and optionally a portion of the monomer(s). The remaining monomer(s) is placed into a separate vessel. Initiator is dissolved or suspended in the reaction medium in still another separate vessel. The medium in the reactor is heated and stirred while the monomer+medium and initiator+medium are introduced over time, for example by a syringe pump or other pumping device. The rate and duration of feed is determined largely by the quantity of solution the desired monomer/chain transfer agent/initiator ratio and the rate of the polymerization. When the feed is complete, heating can be continued for an additional period.

Following completion of the polymerization, the polymer can be isolated by stripping off the medium and unreacted monomer(s) or by precipitation with a non-solvent. Alternatively, the polymer solution/emulsion can be used as such, if appropriate to its application. The applications for the S-(α,α'-disubstituted-α"-acetic acid) dithiocarbamate compounds include any of those listed hereinabove with regard to the trithiocarbonate compounds.

Derivatives of the dithiocarbamate polymers or copolymers can also be formed including esterification products from the alcohol and/or diol end groups present. Thioesters can be formed utilizing mercaptan, and amides can be formed from amines, etc. Ammonium salts can be formed from primary, secondary, and tertiary amines. Metal salts can be formed from alkaline or alkaline earth hydroxides, oxides and the like.

The invention has wide applicability in the field of free radical polymerization and can be used to produce polymers and compositions for coatings, including clear coats and base coat finishes for paints for automobiles and other vehicles or industrial, architectural or maintenance finishes for a wide variety of substrates. Such coatings can further include conventional additives such as pigments, durability agents, corrosion and oxidation inhibitors, rheology control agents, metallic flakes and other additives. Block, star, and branched polymers can be used as compatibilizers, thermoplastic elastomers, dispersing agents or rheology control agents. Additional applications for polymers of the invention are in the fields of imaging, electronics (e.g., photoresists), engineering plastics, adhesives, sealants, paper coatings and treatments, textile coatings and treatments, inks and overprint varnishes, and polymers in general.

Alkoxy Dithiocarbonates

Yet another embodiment of the present invention relates to alkoxy dithiocarbonate compounds having the following formula:

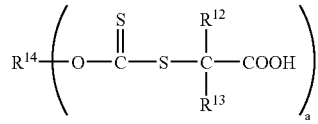

wherein $R^2$, $R^3$, and $R^{14}$ are as defined hereinabove, and wherein "a" is 1 to about 4 with 1 or 2 preferred.

The compounds of the above formula can also be generally identified as O-alkyl-S-(α,α'-disubstituted-α"-acetic acid) xanthates. The O-alkyl-S-(α,α'-disubstituted-α"-acetic acid) xanthates are generated as the reaction product of an alkoxylate salt, carbon disulfide, a haloform, and a ketone. Alternatively, a metal salt of xanthate can be utilized in place of the alkoxylate salt and carbon disulfide.

The alkoxylate salt or carbon disulfide, or alternatively the metal salt of xanthate are typically the limiting agents for the reaction. The haloform is utilized in the reaction in an amount generally from 0 percent to about 500 percent molar excess, and preferably from about 50 to about 200 percent molar excess. The ketone is utilized in the reaction in an amount generally from 0 percent to about 3000 percent molar excess, and preferably from about 100 percent to about 1000 percent molar excess. The metal hydroxide when utilized, is present in an amount from 10 percent to 500 percent molar excess, with about 60 percent to 150 percent molar excess preferred.

The general reaction mechanism for forming the O-alkyl-S-(α,α'-disubstituted-α"-acetic acid) xanthates is as follows:

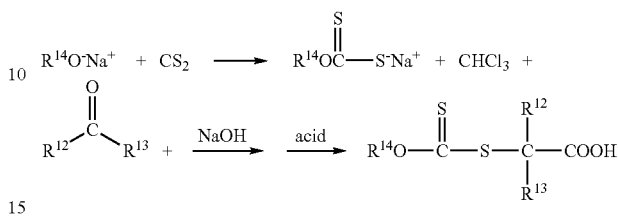

The preparation of the O-alkyl-S-(α,α'-disubstituted-α"-acetic acid) xanthates begins with the addition of a xanthate, i.e., a salt of xanthic acid to a reaction vessel, preferably equipped with an agitating device, thermometer, addition funnel, and a condenser. The xanthate can be prepared from an alkoxylate salt and carbon disulfide as known in the art.

For example, the sodium salt of O-ethyl xanthate, $CH_3CH_2OC(S)S^-Na^+$, can be prepared from sodium ethoxide and carbon disulfide in the presence of a solvent such as an acetone, and optionally a catalyst, such as Aliquot 336 or other catalyst stated herein or known in the art, in a reaction vessel, preferably at about 0° to about 25° C. The general reaction is:

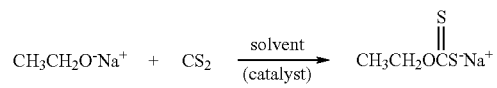

The metal salt of O-ethyl xanthate is also commercially available from sources such as Aldrich Chemical of Milwaukee, Wis.

In a further step, a ketone, a haloform, optionally a solvent, and a catalyst, all as described hereinabove, are added to the reaction vessel containing the xanthate metal salt. When the ketone is used as the solvent, the catalyst is optionally eliminated from the process. A strong base as noted hereinabove is added to the mixture, preferably over an extended period of time. The reaction components are preferably mixed throughout the reaction. The reaction product is subsequently acidified with an acid as noted hereinabove, completing the reaction and forming the O-alkyl-S-(α,α'-disubstituted-α"-acetic acid) xanthate. The reaction is conducted at a temperature generally from about 0° C. to about 80° C., and preferably from about 15° C. to about 50° C., with room temperature being preferred. The reaction can be performed at atmospheric pressure under an inert atmosphere. The reaction time generally depends on temperature, and generally is complete within 20 hours, and preferably within 10 hours. An α-trihalomethyl-α-alkanol can be utilized in place of a haloform and ketone, as noted hereinabove with regard to the trithiocarbonate compounds.

The O-alkyl-S-(α,α'-disubstituted-α"-acetic acid) xanthates can be utilized as an initiator to initiate or start the polymerization of a monomer, as a chain transfer agent which interrupts and terminates the growth of a polymer chain by formation of a new radical which can act as the nucleus for forming a new polymer chain, and/or as a terminator which are incorporated into a polymer as a dormant species. Preferably, the O-alkyl-S-(α,α'-disubstituted-α"-acetic acid) xanthates are utilized as chain transfer agents in free radical polymerizations having living characteristics to provide polymers of controlled molecular weight and low polydispersity.

Xanthate (Co)Polymers

Polymers or copolymers of the following formulas can be prepared from the O-alkyl-S-(α,α'-disubstituted-α"-acetic acid) xanthates:

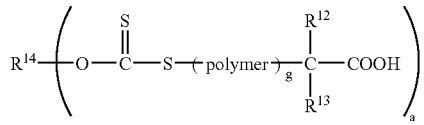

wherein a, $R^{12}$, $R^{13}$, and $R^{14}$ are as defined hereinabove, wherein the polymer is derived from a conjugated diene monomer, or a vinyl containing monomer, or combinations thereof, as defined hereinabove and incorporated by reference, and wherein each g repeat unit, independently, is the same or different and is generally from 1 to about 10,000, and preferably from about 5 to about 500. Preferred monomers are alkyl acrylates, acrylic acid, and styrene. Of course, it is to be understood that when g is 1, the polymer is a single reacted monomer unit.

The above polymers or copolymers can be prepared by bringing into contact with each other the monomer(s) which form O-alkyl-S-(α,α'-disubstituted-α"-acetic acid) xanthate compound, and optionally a) solvent, and b) a radical polymerization initiator; in suitable amounts, as described hereinabove.

It is believed the mechanism is as follows:

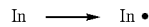

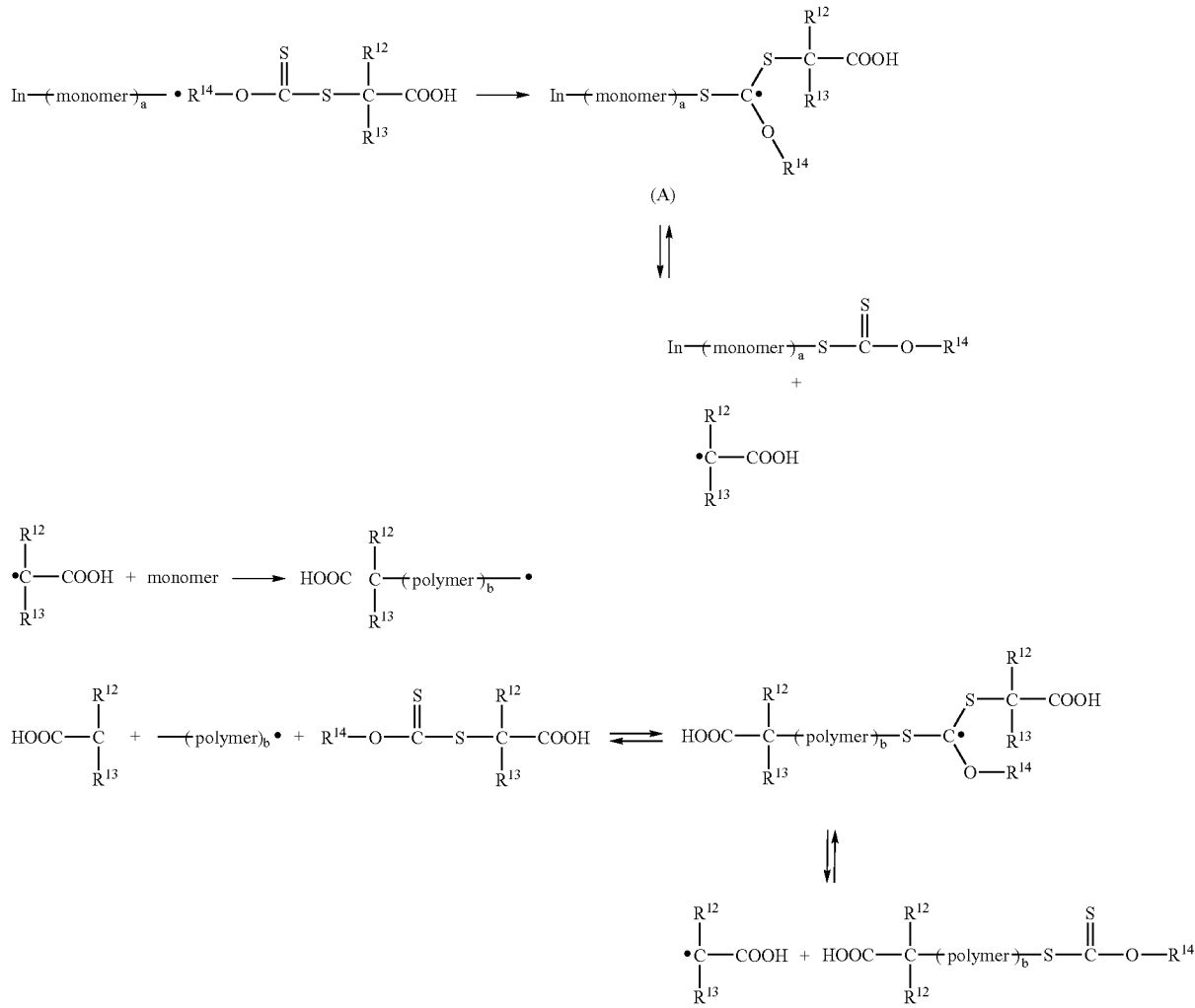

As illustrated by the above mechanism, the monomers are polymerized into the xanthate compounds adjacent to the thiocarbonylthio linkage, between the single bonded sulfur atom and the tertiary carbon atom of the compound.

The O-alkyl dithiocarbonate compounds of the present invention can be used to produce polymers which are substantially colorless. The polymers or copolymers of the O-alkyl dithiocarbanate compounds are more hydrolytically stable because the electro-donating amino groups render the thiocarbonyl group less electrophilic and the polymers are stable toward nucleophiles such as amines.

The reaction conditions are chosen as known to one skilled in the art so that the temperature utilized will generate a radical in a controlled fashion, wherein the temperature is generally from about room temperature to about 200° C. The reaction can be performed at temperatures lower than room temperature, but it is impractical to do so. The temperature often depends on the initiator chosen for the reaction, for example, when AIBN is utilized, the temperature generally is from about 40° C. to about 80° C., when azodicyanodivaleric acid is utilized, the temperature generally is from about 50° C. to about 90° C., when di-t-butylperoxide is utilized, the temperature generally is from about 110° C. to about 160° C., and when O-alkyl-S-($\alpha,\alpha'$-disubstituted-$\alpha''$-acetic acid) xanthate is utilized, the temperature is generally from about 80° C. to about 200° C.

As noted above with respect to the dithiocarbamate compounds, the polymers or copolymers prepared from the O-alkyl-S-($\alpha,\alpha'$-disubstituted-$\alpha''$-acetic acid) xanthate contain reactive end groups which are able to further undergo chemical transformation or reaction in order to be joined with another polymer chain, in order to form extended copolymers for example. The process of the invention can be carried out, for example, in emulsion solution or suspension in either a batch, semi-batch, continuous, bulk or feed mode.

Conventional procedures can be used to produce narrow polydispersity polymers. For lowest polydispersity polymers, the chain transfer agent is added before polymerization is commenced. The polydispersity of the xanthate polymers or copolymers is generally less than about 3.0. For example, when carried out in batch mode in solution, the reactor is typically charged with chain transfer agent and monomer or medium plus monomer. The desired amount of initiator is then added to the mixture and the mixture is heated for a time which is dictated by the desired conversion and molecular weight. Polymers with broad, yet controlled, polydispersity or with multimodal molecular weight distribution can be produced by controlled addition of the chain transfer agent over the course of the polymerization process.

In the case of emulsion or suspension polymerization the medium will often be predominately water and the conventional stabilizers, dispersants and other additives can be present. For solution polymerization, the reaction medium can be chosen from a wide range of media to suit the monomer(s) being used.

As already stated, the use of feed polymerization conditions allows the use of chain transfer agents with lower transfer constants and allows the synthesis of block polymers that are not readily achieved using batch polymerization processes. If the polymerization is carried out as a feed system the reaction can be carried out as follows. The reactor is charged with the chosen medium, the chain transfer agent and optionally a portion of the monomer(s). The remaining monomer(s) is placed into a separate vessel. Initiator is dissolved or suspended in the reaction medium in another separate vessel. The medium in the reactor is heated and stirred while the monomer+medium and initiator+medium are introduced over time, for example by a syringe pump or other pumping device. The rate and duration of feed is determined largely by the quantity of solution the desired monomer/chain transfer agent/initiator ratio and the rate of the polymerization. When the feed is complete, heating can be continued for an additional period.

Following completion of the polymerization, the polymer can be isolated by stripping off the medium and unreacted monomer(s) or by precipitation with a non-solvent. Alternatively, the polymer solution/emulsion can be used as such, if appropriate to its application. The applications for the O-alkyl-S-($\alpha,\alpha'$-disubstituted-$\alpha''$-acetic acid) xanthate dithiocarbonate compounds include any of those listed hereinabove with regard to the trithiocarbonate and dithiocarbamate compounds.

The dithiocarbonate compounds of the invention have wide applicability in the field of free radical polymerization and can be used as thickeners and to produce polymers and compositions for coatings, including clear coats and base coat finishes for paints for automobiles and other vehicles or industrial, architectural or maintenance finishes for a wide variety of substrates. Such coatings can further include pigments, durability agents, corrosion and oxidation inhibitors, rheology control agents, metallic flakes and other additives. Block and star, and branched polymers can be used as compatibilizers, thermoplastic elastomers, dispersing agents or rheology control agents. Additional applications for polymers of the invention are composites, potting resins, foams, laminate, in the fields of imaging, electronics (e.g., photoresists), engineering plastics, adhesives, sealants, paper coatings and treatments, textile coatings and treatments, inks and overprint varnishes, and polymers in general, and the like.

The present invention will be better understood by reference to the following examples which serve to describe, but not to limit, the present invention.

EXAMPLES

Example 1

Synthesis of s,s'-bis-($\alpha$, $\alpha'$-disubstituted-$\alpha''$-acetic acid)-trithiocarbonate, ($R^1=R^2=CH_3$)

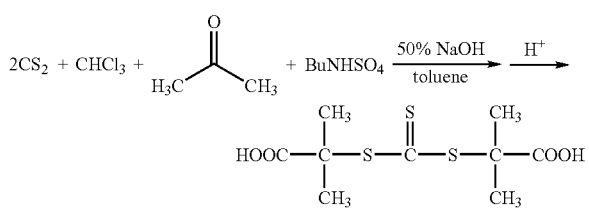

Procedure:

In a 500 ml jacketed flask equipped with a mechanical stirrer, a thermometer, a reflux condenser and an addition funnel added 22.9 grams of carbon disulfide, 2.0 gram of tetrabutylammonium bisulfate and 100 ml toluene. The solution was stirred at 20° C. under nitrogen and 168 grams of 50% sodium hydroxide solution was added dropwise to keep the temperature between 20–30° C. 30 min. after the addition, a solution of 43.6 grams of acetone and 89.6 grams of chloroform was added at 20–30° C. The reaction was then stirred at 15–20° C. overnight. 500 ml water was added to the mixture, the layers were separated. The organic layer was discarded and the aqueous layer was acidified with concentrated HCl to precipitate the product as yellow solid. 50 ml toluene was added to stir with the mixture. Filtered and rinsed the solid with toluene to collect 22.5 grams of product after drying in the air to constant weight.

Example 2

Synthesis of s,s'-bis-(α, α'-disubstituted -α''-acetic acid) trithiocarbonates. ($R^1=R^2=CH_3$)

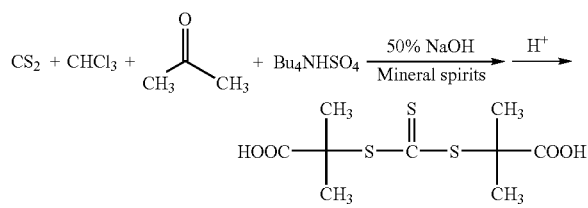

The procedure was essentially the same as in example 1, except that mineral spirits replaced toluene as solvent. 40.3 grams of product was obtained as yellow solid.

Example 3

Synthesis of s-alkyl-s'-(-(α, α'-disubstituted-α''-acetic acid)-trithiocarbonates

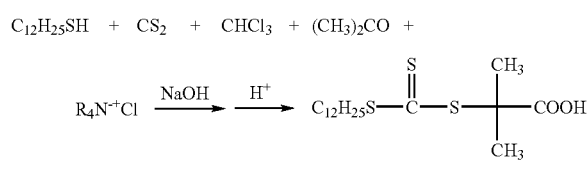

Procedure:

Dodecylmercaptan (0.1 mole), and Aliquot 336 (0.004 mole) was dissolved in 48 g acetone. 50% sodium hydroxide solution (0.105 mole) was added, followed by dropwise addition of carbon disufide (0–1 mole) in 10 g acetone solution. The media turned from colorless to yellow. After 20 min., chloroform (0.15 mole) was added followed by dropwise addition of 50% NaOH (0.5 mole) and 5 g NaOH beads. The rxn was stirred at 15–20° C. overnight, filtered and the sol. was rinsed with acetone. The acetone layer was concentrated to dryness. The mass was dissolved in water, acidified with concentrated HCl to precipitate the product, rinsed with water to collect the yellow solid. The solid was dissolved in 350 ml hexanes. The solution was dried over magnesium sulfate and filtered. The organic solution was cooled to precipitate the product as yellow flakes. Yield is 85%.

Example 4

Polymerization of Prior Art Compounds

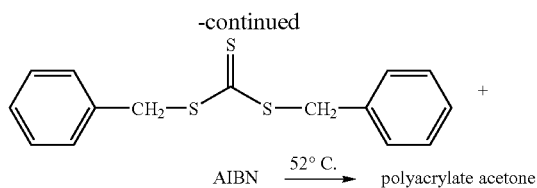

Procedure:

Dibenzyltrithiocarbonate (1.54 g, 5.3 mmole), 2-ethyl-hexylacrylate (25 grams 135.7 mmole), AIBN (0.05 g, 0.3 mmole) and acetone (25 ml) were mixed.

1 ml of undecane was added as GC internal standard for calculating the conversion. The solution was purged with nitrogen for 15 min. before heating to 52° C. under nitrogen. No exotherm was detected throughout the reaction. Aliquots of the sample were taken for GC and GPA analyses during the course of the polymerization. The following table showed the progress of the polymerization in 7 hours.

| Sample | Time (mins.) | Mn | Mw | Conv. % |
|---|---|---|---|---|
| 1 | | | | |
| 2 | 120 | 866 | 970 | 3.7 |
| 3 | 270 | 1180 | 1428 | 13.2 |
| 4 | 420 | 1614 | 2059 | 26.9 |

Example 5

Polymerization with s,s'-bis-(α, α'-disubstituted-α''-acetic acid)-trithiocarbonates

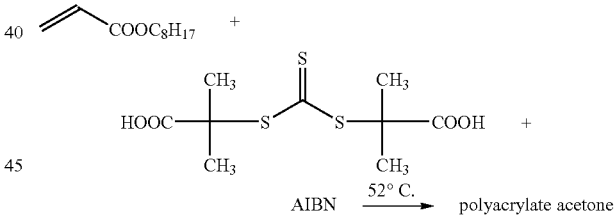

Procedure:

Following the same procedure as in example 4, the novel tricarbonate (1.50 g, 5.3 mmole), 2-ethylhexylacrylate (25 g, 135.7 mmole), AIBN (0.05 g, 0.3 mmole) and acetone (25 ml) were mixed. 1 ml of undecane was added as internal standard The reaction was stirred at 52° C. for 7 hours. The following table showed the conversion and the molecular weights of the resulting polymer.

| Sample | Time (mins.) | Mn | Mw | Conv. % |
|---|---|---|---|---|
| 1 | 45 | 669 | 724 | 3.5 |
| 2 | 120 | 1433 | 1590 | 25.8 |
| 3 | 240 | 3095 | 3621 | 79.8 |
| 4 | 300 | 3345 | 3898 | 87.9 |
| 5 | 420 | 3527 | 4136 | 93.9 |

Example 6

Polymerization with s,s'-bis-(α, α'-disubstituted-α''-acetic acid) trithiocarbonates

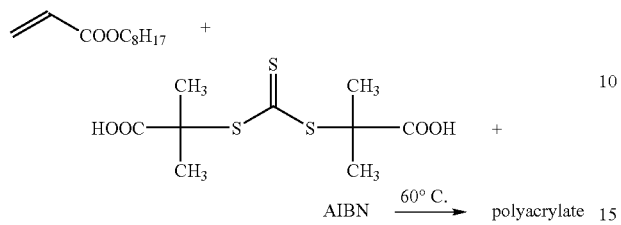

Procedure:

This is a bulk polymerization with the trithiocarbonate as chain-transfer agent The trithiocarbonate (1.0 g, 3.5 mmole), 2-ethylhexylacrylate (25 g, 135.7 mmole), AIBN (0.05 g, 0.3 mmole) and 1 ml undecane (internal standard) were purged with nitrogen, then heated to 60° C. for 3 hours. The following table showed the conversion and the molecular weight of the polymer.

| Sample | Time (mins.) | Mn | Mw | Conv. % |
|---|---|---|---|---|
| 1 | 30 | 2229 | 2616 | 35.6 |
| 2 | 90 | 4501 | 5526 | 91.9 |
| 3 | 180 | 4672 | 5780 | 97.8 |

Example 7

Polymerization with s,s'-bis-(α, α'-disubstituted-α''-acetic acid) trithiocarbonates

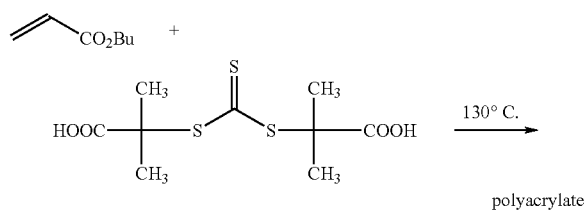

Procedure:

The trithiocarbonate was used as inifertor. Trithiocarbonate (1.0 g, 3.5 mmole), n-butylacrylate (20 g, 156.1 mmole) with 1 ml decane as internal standard were purged with nitrogen for 15 min., then polymerized at 130° C. under nitrogen for 6 hours. The following table showed the conversion and the molecular weights of the polymer.

| Sample | Time (mins.) | Mn | Mw | Conv. % |
|---|---|---|---|---|
| 1 | 60 | 1118 | 1242 | 16.0 |
| 2 | 120 | 1891 | 2199 | 32.5 |
| 3 | 240 | 2985 | 3337 | 52.5 |
| 4 | 360 | 3532 | 4066 | 65.7 |

Example 8

Free Radical Polymerization Utilizing s,s'-bis-(α, α'-disubstituted-α''-acetic acid)-trithiocarbonates as Inifertor

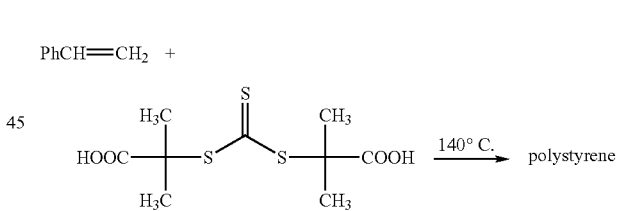

Procedure:

The trithiocarbonate (2.0 g, 7.1 mmole) and 2-ethylhexylacrylate (25.0 g, 135.7 mmole) were purged with nitrogen for 15 min then heated to 175° C. for 10 hours. The following table showed the conversion and molecular weighs of the polymer.

| Sample | Time (mins.) | Mn | Mw | Conversion |
|---|---|---|---|---|
| 1 | 40 | 1006 | 1117 | 24.2 |
| 2 | 90 | 1446 | 1699 | 42.0 |
| 3 | 150 | 1750 | 2241 | 51.9 |
| 4 | 600 | 2185 | 3115 | 98.9 |

Example 9

Polymerization with s,s'-bis-(α, α'-disubstituted-α''-acetic acid) trithiocarbonates PhCH═CH₂ +

Procedure:

The trithiocarbonate was used as inifertor to make polystyrene. The trithiocarbonate (2.0 g, 7.1 mmole) and styrene (25 g, 240.4 mmole) with 1 ml decane as internal standard were polymerized at 140° C. under nitrogen for 6 hours. The following table showed the progress of the polymerization.

| Sample | Time (mins.) | Mn | Mw | Conv. % |
|---|---|---|---|---|
| 1 | 30 | 613 | 648 | 9.5 |
| 2 | 60 | 779 | 831 | 16.9 |
| 3 | 120 | 1829 | 2071 | 53.9 |
| 4 | 300 | 2221 | 2559 | 72.3 |
| 5 | 360 | 2537 | 2956 | 84.5 |

Example 10

Polymerization with s,s'-bis-(α, α'-disubstituted-α"-acetic acid) trithiocarbonates

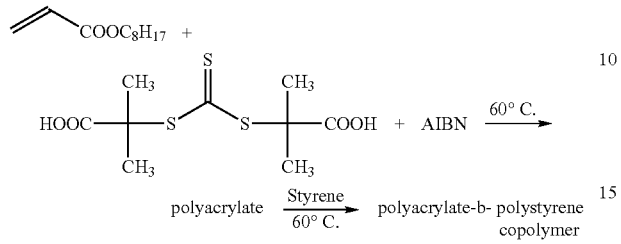

polyacrylate $\xrightarrow[60°\text{ C.}]{\text{Styrene}}$ polyacrylate-b- polystyrene copolymer Procedure:

The trithiocarbonate was used as chain-transfer agent to make block copolymers of 2-ethylhexylacrylate and styrene. The trithiocarbonate (1.5 g, 5.3 mmole), 2-ethylhexylacrylate (30 g, 162.8 mmole) and AIBN (0.03 g, 0.18 mmole) with 1 ml undecane as the internal standard were polymerized at 60° C. under nitrogen as before. 6.5 hours later, styrene (15 g, 144.2 mmole) and AIBN (0.03 g, 0.18 mmole) was added. The polymerization continued and the following shows the progress.

| Sample | Time (mins.) | Mn | Mw | Conv. % |
|---|---|---|---|---|
| 1 | 70 | 1922 | 2459 | 32.5 |
| 2 | 135 | 3556 | 4204 | 80.8 |
| 3 | 270 | 4095 | 4874 | 95.0 |
| 4 | 330* | 4407 | 5025 | 96.6 |
| 5 | 1290 | 4834 | 5969 | — |

*Styrene added

Example 11

Polymerization with the trithiocarbonate from example 3. The trithiocarbonate (1.82 g. 5 mmole), n-butyl acrylate (25 g, 195.1 mmole) and AIBN (0.04 g, 0.25 mmole) with 1 ml undecane as the internal standard were polymerized under nitrogen atmosphere for 7 hours. It showed 97.5% conversion by GC as depicted in the following table:

| Sample | Time (min) | Mn | Mw | Pd | % Conv. |
|---|---|---|---|---|---|
| 1 | 60 | 2177 | 2792 | 1.26 | 46.2 |
| 2 | 120 | 2758 | 3865 | 1.40 | 67.1 |
| 3 | 420 | 3786 | 5439 | 1.44 | 97.5 |

Example 12

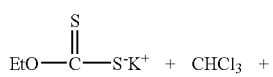 + CHCl₃ +

-continued

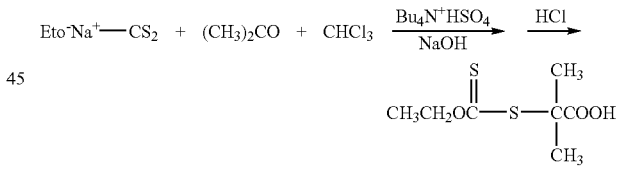

Procedure:

In a 300 ml jacketed flask equipped with a mechanical stirrer, thermometer, addition funnel and nitrogen-inlet tube (for inerting) 16.3 grams potassium O-ethylxanthate, 17.9 grams chloroform, 1.36 grams tetrabutylammonium hydrogen sulfate and 88.1 grams cyclohexanone were placed and cooled to between 15–20° C. 40 grams of sodium hydroxide beads were added in portions to keep the temperature below 25° C. After the addition, the reaction was stirred at about 20° C. for 12 hours. 100 ml of water was added and the aqueous layers were acidified with concentrated hydrochloric acid. 100 ml toluene was added to extract the product. After drying the toluene solution with magnesium sulfate, it was filtered and concentrated to afford 20 grams of yellow solid which was further purified by recrystallizing from hexanes.

Example 13

$$\text{Eto}^-\text{Na}^+ \text{—} CS_2 + (CH_3)_2CO + CHCl_3 \xrightarrow[\text{NaOH}]{\text{Bu}_4\text{N}^+\text{HSO}_4^-} \xrightarrow{\text{HCl}}$$

$$\underset{\underset{\text{CH}_3\text{CH}_2\text{OC}}{\overset{\overset{S}{\parallel}}{}}}{}\text{—}S\text{—}\underset{\underset{CH_3}{|}}{\overset{\overset{CH_3}{|}}{C}}\text{COOH}$$

In this example, sodium O-ethylxanthate was formed in situ. 7.6 grams carbon disulfide, 1 gram tetrabutylammonium hydrogen sulfate and 58.1 grams acetone were stirred in a reaction vessel as equipped above in Example 12. 7.1 grams sodium ethoxide (96%, Aldrich) was added in portions at room temperature. 30 minutes after the addition, 17.9 grams chloroform was added followed by 20 grams sodium hydroxide beads in portions to keep the temperature below 25° C. Stirred at 15° C. for 12 hours. The mixture was filtered and rinsed thoroughly with acetone. The acetone solution was concentrated and dissolved in water. 20 ml concentrated HCl was added. The oil formed was extracted into two 50 ml portions of toluene, dried over magnesium sulfate, and concentrated into an oil. The oil was extracted with two 50 ml portions of boiling hexane. Beige-colored solid was produced from the solution.

Example 14

Synthesis of S-(methyl, methyl, acetic acid) dithiocarbamate

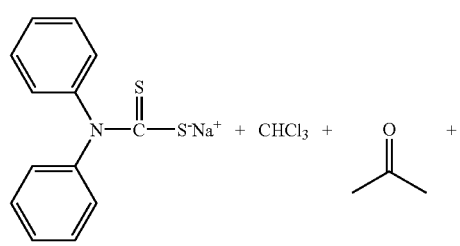

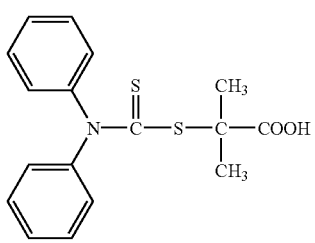

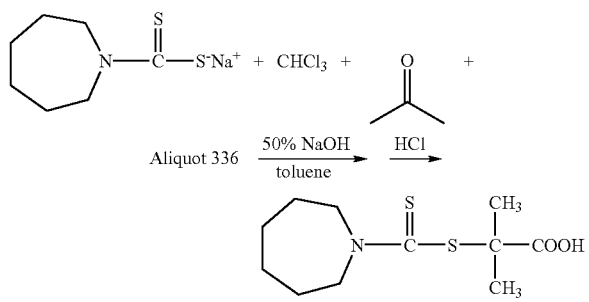

Procedure:

10.7 grams sodium N,N-diphenyldithiocarbamate, 7.2 grams chloroform, 4.6 grams acetone, 0.8 gram Aliquot 336 and 50 ml toluene were stirred at 15–20° C. under nitrogen while 16 grams 50% sodium hydroxide was added dropwise to keep the reaction temperature below 20° C. The reaction was stirred for 12 hours. Water was added to dissolve the solid. The layers were separated and the aqueous layer was acidified with concentrated hydrochloric acid. The solid was washed with water and recrystallized from toluene to afford light-yellow colored solid.

Example 15

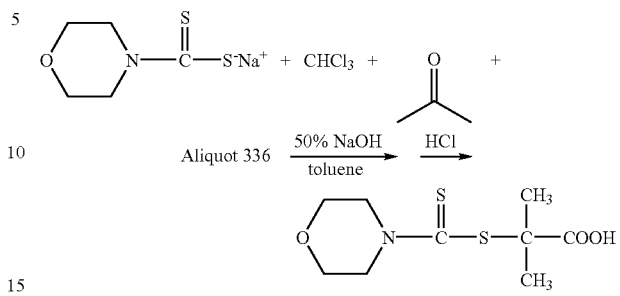

Procedure:

Sodium N,N-diphenyldithiocarbamate was replaced by sodium N,N-hexamethylenedithiocarbamate and the reaction was conducted as explained in Example 14. The product was a white solid.

Example 16

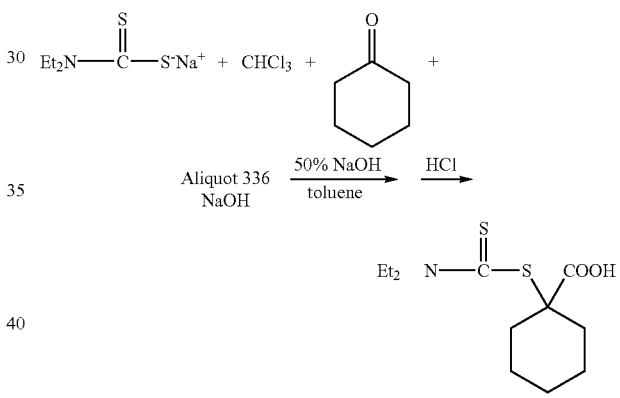

Procedure:

The sodium dithiocarbamate utilized in this example was sodium morpholinodithiocarbamate. The reaction was conducted as explained in Example 14. The product was afforded in good yield as white powders.

Example 17

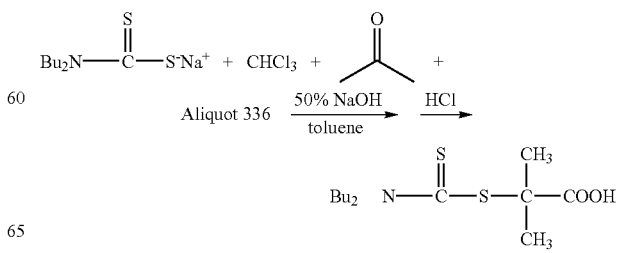

Procedure:

The sodium dithiocarbamate utilized in this example was sodium N,N-diethyl dithiocarbamate. The reaction was conducted as explained in Example 14 and acetone was replaced by cyclohexanone. The product was afforded in good yield as white powders.

Example 18

Procedure:

Sodium N,N-dibutyldithiocarbamate was utilized in this example. The reaction was conducted as described in Example 14. The product was isolated as white powder.

Example 19

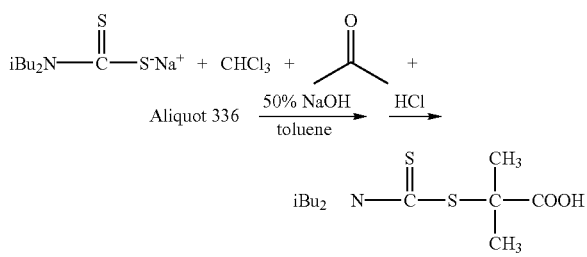

Procedure:

Sodium N,N-di-isobutyldithiocarbamate was utilized in this example. The reaction was conducted as described in Example 14. The product was isolated as yellow solid.

Example 20

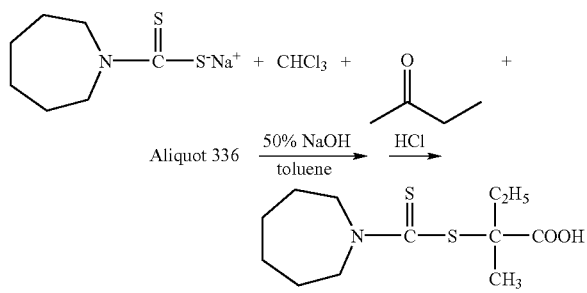

Procedure:

Sodium N,N-hexamethylene dithiocarbamate, 2-butanone was utilized in this example. The reaction was conducted as explained in Example 14 and was replaced by acetone. The product was afforded in good yield as white powder after recrystallization from hexane/toluene.

Example 21

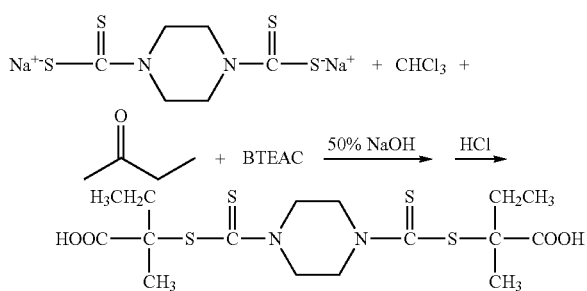

Procedure:

14.1 grams of S,S'-disodium salt of the piperazine bis-(dithiocarbamic acid), 100 ml 2-butanone, 17.9 grams chloroform and 1.13 grams benzyltriethylammonium chloride were mixed and stirred at 15–20° C. under nitrogen atmosphere. 40 grams 50% sodium hydroxide solution was added in portions to keep the reaction temperature under 20° C. After the addition, the reaction was allowed to stir at 20° C. for 12 hours. The mixture was filtered and the solid was rinsed with 2-butanone and then stirred with 100 ml water. Concentrated HCl was added until water turned acidic. The solid was collected and rinsed with water, to yield off-white colored powders. The powder was crystallized with methanol to afford white powder.

Example 22

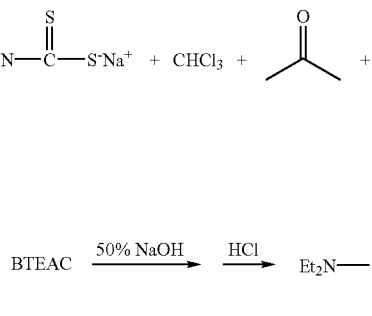

As in the above procedure of Example 21 the disodium salt of piperizine bis-(dithiocarbamic acid) was replaced with sodium diethyldithiocarbamate, and 2-butanone with acetone. The desired product was obtained as white powders in high yield.

Example 23

The procedure of Example 21 was utilized and the disodium salts of piperizine bis-(dithiocarbamic acid) was replaced by sodium dimethyldithiocarbamate, and BTEAC was replaced by tetrabutylammonium hydrogensulfate, the desired product was obtained as white powders.

Example 24

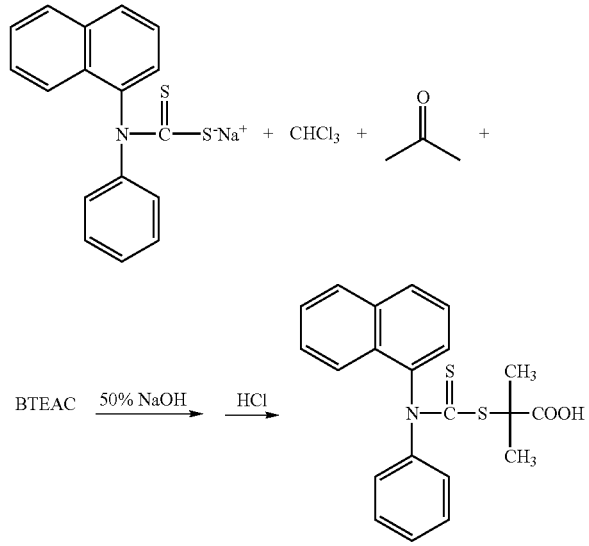

The reaction was performed as in Example 21, but the dithiocarbamate salt was sodium N-phenyl-N-1-naphthyl dithiocarbamate, and the ketone was acetone. The product was obtained as beige-colored powders after recrystallization from a mixture of toluene and heptane.

Example 25

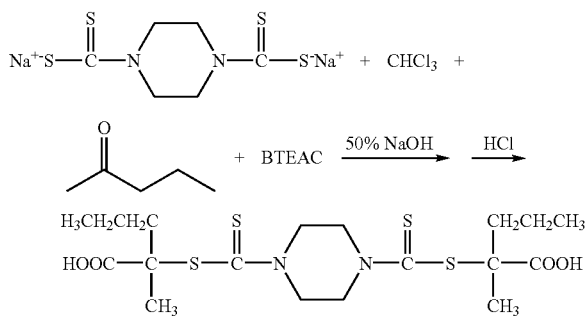

The reaction was performed in a similar manner as in Example 21, but 2-butanone was replaced by 2-pentanone, the product was white powders after recrystallization from hexanes.

Example 26

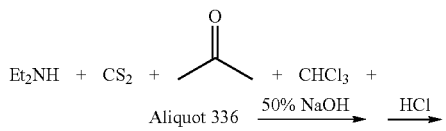

-continued

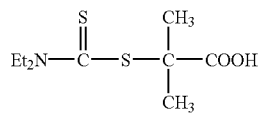

Procedure:

7.38 grams diethylamine and 80 ml acetone and 2.0 grams Aliquot 336 were mixed and stirred under nitrogen atmosphere at 15° C. 7.6 grams carbon disulfide in 20 ml acetone was added dropwise to keep the temperature below 20° C. 30 minutes after the addition, 8.8 grams 50% sodium hydroxide was added. 30 minutes later, 17.9 grams chloroform was added followed by 31.2 grams 50% sodium hydroxide. The reaction was allowed to stir at 15–20° C. for 12 hours. The mixture was concentrated and then dissolved in water. 15 ml concentrated HCl was added to precipitate a beige-colored solid which was washed thoroughly with water (20 grams). Recrystallization from toluene afforded white solid.

Example 27

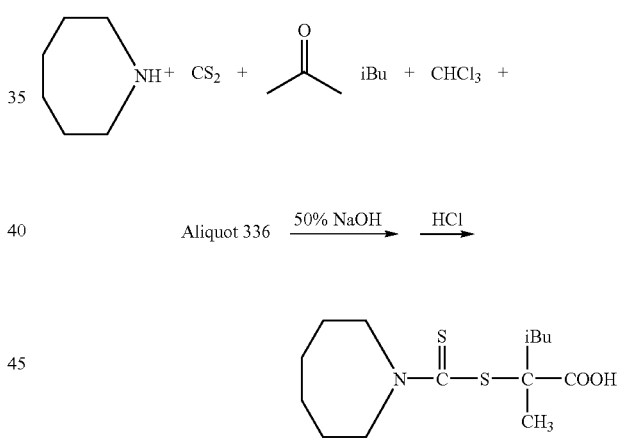

Procedure:

The diethylamine of the procedure of Example 26 was replaced by hexamethyleneimine and acetone was replaced by methyl isobutyl ketone. The product was recrystallized from hexane/toluene to afford white powders.

Example 28

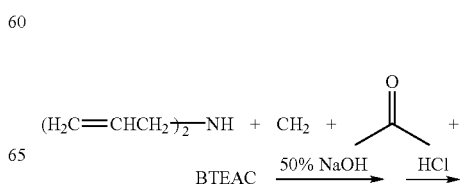

-continued

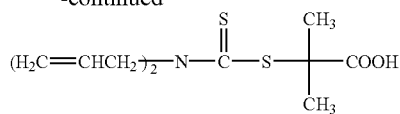

The diethylamine of the procedure of Example 26 was replaced by diallylamine and Aliquot® 336 was replaced by BTEAC. The product was white crystalline solid after recrystallization from hexane/toluene.

Example 29

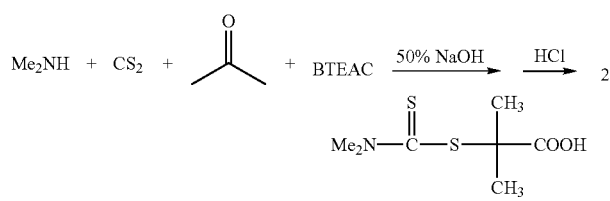

The diethylamine of the procedure of Example 26 was replaced by dimethyl-amine (40% in water). The product was white crystals after recrystallization from toluene.

Example 30

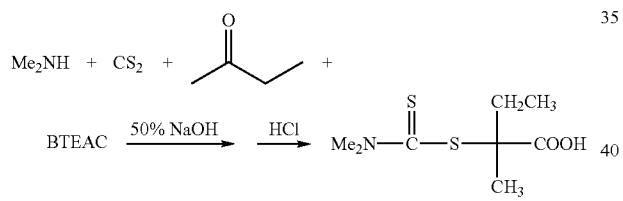

The acetone of the procedure of Example 27 was replaced by 2-butanone. The produce was a white solid after recrystallization from toluene.

Example 31

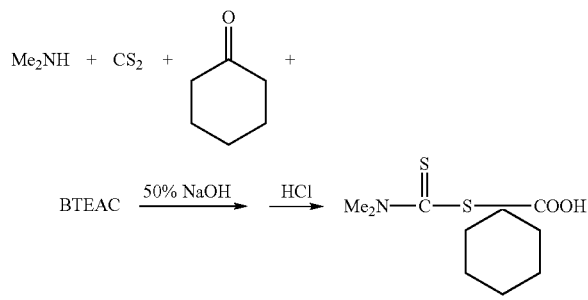

The acetone of the procedure of Example 26 was replaced by cyclohexanone. The product was white solid after recrystallization from toluene.

Example 32

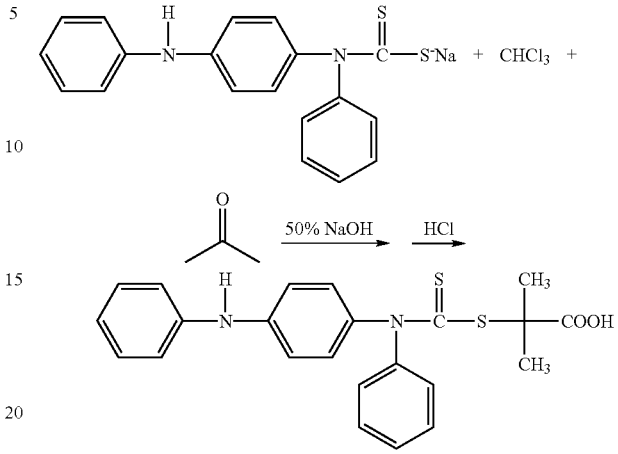

In this example, 22.8 grams of sodium N-phenyl-N-4-anlinophenyl dithiocarbamate, 17.9 grams chloroform and 100 ml acetone were mixed and stirred at 150° C. under nitrogen. 40 grams 50% sodium hydroxide was added dropwise in to keep the temperature under 20° C. The reaction was allowed to stir overnight (approximately 12 hours) at 15° C. Solvent was removed in a rotary evaporator and the residue was dissolved in water. The aqueous solution was acidified with concentrated hydrochloric acid to collect a green-colored solid. The dried solid was recrystallized from toluene to afford grayish-colored solid. The structure was confirmed by H-NMR.

Example 33

Controlled Radical Polymerization with Novel Dithiocarbonate Derivatives

The theoretical number-averaged molecular $(Mn)_{theo}$ weight for each polymer or copolymer was calculated from the formula XII (a) assuming 100% conversion. $(Mn)_{ex}$ is the Mn measured by GPC from polymerization products. In bulk polymerization, 20–25 grams of monomer, 0.01–0.05 grams of an initiator such as AIBN and the amount of the dithiocarbonate as needed to give desired Mn (calculated using formula XII(a)) are purged with nitrogen gas, then heated to temperature gradually. Sometimes air or water-cooling is necessary to keep the temperature under 83° C. The resulting polymers were subjected to MALDI mass spectrum measurement. The spectrum clearly showed the carboxyl-terminating group in every polymer chain.

Block copolymerization was performed by making the first polymer in bulk, then add the second monomer and same amount of initiator, then polymerizing in the same manner. Random copolymerization could have been performed if both monomers were added at the same time.

The results of the polymerizations and block polymerizations are listed in the following table.

| Dithiocarbonate Polymers | | | | | | | |
|---|---|---|---|---|---|---|---|
| Dithiocarbonate Example | Monomer | Solvent | Temp. | $(Mn)_{ex}$ | $(Mn)_{theo}$ | PD | Time/ Hour |
| Control | Butyl acrylate | — | | >100,000 | | >3 | 1 |
| 12 | Butyl acrylate | MEK | 80 | 3777 | 5000 | 1.78 | 5 |
| 26 | Styrene | none-bulk polym. | 140 | 7830 | 5000 | 2.05 | 5 |
| 17 | Butyl acrylate | MEK | 80 | 1645 | 2000 | 2.07 | 5 |
| 14 | Butyl acrylate | MEK | 75 | 4656 | 5000 | 1.31 | 5 |
| 21 | Butyl acrylate | MEK | 80 | 3049 | 3000 | 1.32 | 6 |
| 19 | Butyl acrylate | MEK | 80 | 3683 | 3000 | 2.03 | 6 |
| 13 | Ethyl acrylate | none-bulk polym. | 65 | 5564 | 10000 | 1.83 | 5 |
| 29 | Vinyl acetate | none-bulk polym. | 70 | 4367 | 5000 | 1.47 | 5 |
| 15 | t-butylacrylamide | THF | 70 | 3622 | 5000 | 1.91 | 5 |
| 24 | Butyl acrylate | none-bulk polym. | 80 | 5093 | 5000 | 1.36 | 6.5 |
| 32 | Butyl acrylate | MEK | 80 | 2061 | 5000 | 1.61 | 2.5 |

| Block Copolymers | | | | | | | |
|---|---|---|---|---|---|---|---|
| Dithiocarbonate Example | Monomer-1 | $(Mn)_{ex}$ | $(Mn)_{theo}$ | PD | Monomer-2 | $(Mn)_{ex}$ | $(Mn)_{theo}$ | PD |
| 30 | Butyl acrylate | 1695 | 1798 | 1.92 | Vinyl acetate | 1873 | 2540 | 1.87 |
| 31 | Butyl acrylate | 1631 | 1798 | 2.23 | Vinyl acetate | 2014 | 2444 | 1.96 |

While in accordance with the patent statutes the best mode and preferred embodiment have been set forth, the scope of the invention is not limited thereto, but rather by the scope of the attached claims.

What is claimed is:

1. A composition, comprising:
an alkoxy dithiocarbonate compound having the formula:

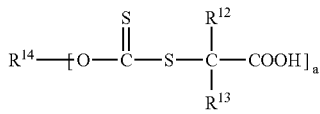

wherein $R^{12}$ and $R^{13}$, independently, can be the same or different, can be optionally substituted, can be a linear or branched alkyl having from 1 to 12 carbon atoms; or an aryl group having from 6 to 18 carbon atoms; or $R^{12}$ and $R^{13}$ can form or be a part of a substituted or unsubstituted cyclic ring having from 3 to 12 carbon atoms, wherein said substituted groups above are independently selected from alkyl having from 1 to 6 carbon atoms; an aryl group; a halogen; a cyano group; an ether having a total of from 2 to about 20 carbon atoms; a nitro; and combinations thereof;
wherein $R^{14}$ is optionally substituted, and can be a linear or branched alkyl having from 1 to 12 carbon atoms, an aryl group optionally saturated or unsaturated; an arylalkyl having from about 7 to 18 carbon atoms; an acyl group; an alkene group; an alkenealkyl having from 3 to 18 carbon atoms; an alkylene group; an alkoxyalkyl; a polyalkylene glycol monoalkyl ether having from 3 to 200 carbon atoms; a polyalkylene glycol monoaryl ether having from 3 to 200 carbon atoms, a 2-trifluoroethyl group, wherein said substituted groups are selected from an alkyl having from 1 to 6 carbon atoms; an aryl; a halogen; a cyano group; an amino group; an alkene group; an alkoxycarbonyl group; an aryloxycarbonyl group; a carboxy group; an acyloxy group; a carbamoyl group; an alkylcarbonyl group; an alkylarylcarbonyl group; an arylcarbonyl group; an arylalkylcarbonyl group; a phthalimido group; a maleimido group; a succinimido group; an amidino group; a guanidimo group; an allyl group; an epoxy group; an alkoxy group; an alkali metal salt; a quaternary ammonium salt; a hydroxyl group; an ether having a total of from 2 to about 20 carbon atoms; a nitro group; a sulfur group; a phosphorous group; a carboalkoxy group; and combinations thereof;
wherein "a" is 2 to about 4.

2. A composition according to claim 1, wherein $R^{12}$ and $R^{13}$, independently, are a phenyl group or an alkyl group having 1 to 10 carbon atoms, or wherein $R^{12}$ and $R^{13}$ are part of a cyclic ring.

3. A composition according to claim 1, wherein $R^{14}$ is an alkyl having from 1 to 8 carbon atoms.

4. A composition according to claim 1, wherein "a" is 2.

5. A composition of claim 1 wherein said composition is an initiator, chain transfer agent or inifertor.

6. A composition according to claim 1, wherein $R^{12}$ and $R^{13}$, independently, are a phenyl group, or an alkyl group having 1 to 10 carbon atoms, or wherein $R^{12}$ and $R^{13}$ are part of a cyclic ring, and wherein $R^{14}$ is an alkyl having from 1 to 8 carbon atoms.

7. A composition of claim 6 wherein said composition is an initiator, chain transfer agent, or inifertor.

8. A composition according to claim 2, wherein $R^{14}$ is an alkyl having from 1 to 4 carbon atoms.

9. A composition according to claim 8, wherein "a" is 2.

10. A composition according to claim 1, wherein "a" is 2 and wherein $R^{12}$ and $R^{13}$, independently, are a phenyl group, or an alkyl group having 1 to 10 carbon atoms, or wherein $R^{12}$ and $R^{13}$ are part of a cyclic ring, and wherein $R^{14}$ is an alkyl having from 1 to 8 carbon atoms.

11. A composition, comprising:
a polymer or copolymer having the formula:

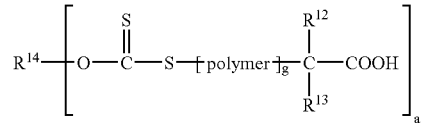

wherein $R^{12}$ and $R^{13}$, independently, can be the same or different, can be optionally substituted, can be a linear or branched alkyl having from 1 to 12 carbon atoms; or an aryl group having from 6 to 18 carbon atoms; or $R^{12}$ and $R^{13}$ can form or be apart of a substituted or unsubstituted cyclic ring having from 3 to 12 carbon atoms, wherein said substituted groups above are independently selected from alkyl having from 1 to 6 carbon atoms; an aryl group; a halogen; a cyano group; an ether having a total of from 2 to about 20 carbon atoms; a nitro; and combinations thereof;

wherein $R^{14}$ is optionally substituted, and can be a linear or branched alkyl having from 1 to about 12 carbon atoms, an aryl group optionally saturated or unsaturated; an arylalkyl having from 7 to 18 carbon atoms; an acyl group; an alkene group; an alkenealkyl having from 3 to 18 carbon atoms; an alkylene group; an alkoxyalkyl; a polyalkylene glycol monoalkyl ether having from about 3 to 200 carbon atoms; a polyalkylene glycol monoaryl ether having from 3 to 200 carbon atoms, a 2-trifluoroethyl group wherein said substituted groups are selected from an alkyl having from 1 to 6 carbon atoms; an aryl; a halogen; a cyano group; an amino group; an alkene group; an alkoxycarbonyl group; an aryloxycarbonyl group; a carboxy group; an acyloxy group; a carbamoyl group; an alkylcarbonyl group; an alkylarylcarbonyl group; an arylcarbonyl group; an arylalkylcarbonyl group; a phthalimido group; a maleimido group; a succinimido group; an amidino group; a guanidimo group; an allyl group; an epoxy group; an alkoxy group; an alkali metal salt; a quaternary ammonium salt; a hydroxyl group; an ether having a total of from 2 to about 20 carbon atoms; a nitro group; a sulfur group; a phosphorous group; a carboalkoxy group; and combinations thereof;

wherein the polymer is derived from at least one $C_1$–$C_{12}$ conjugated diene monomer, or at least one vinyl monomer;

wherein "a" is 1 to about 4; and wherein said at least one vinyl monomer is represented by the formula:

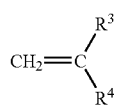

wherein $R^3$ is selected from hydrogen, halogen, $C_1$–$C_4$ alkyl, or substituted $C_1$–$C_4$ alkyl, wherein said substituents, independently, are selected from one or more hydroxy, alkoxy, aryloxy($OR^5$), carboxy, acyloxy, aroyloxy($O_2CR^5$), alkoxy-carbonyl($CO_2R^5$), or aryloxy-carbonyl; N-pyrrolidonyl;

wherein $R^4$ is selected from hydrogen, $R^5$, $CO_2H$, $CO_2R^5$, $COR^5$, CN, $CONH_2$, $CONHR^5$, $O_2CR^5$, $OR^5$ or halogen; and wherein $R^5$ is selected from $C_1$–$C_{18}$ alkyl, substituted $C_1$–$C_{18}$ alkyl, $C_2$–$C_{18}$ alkenyl, aryl, aralkyl, or alkaryl, and wherein said substituents, independently, are selected from one or more epoxy, hydroxy, alkoxy, acyl, acyloxy, carboxy and salts thereof, sulfonic acid and salts thereof, alkoxy- or aryloxy-carbonyl, dicyanato, cyano, silyl, halo or dialkylamino.

12. A composition according to claim 11, wherein $R^{12}$ and $R^{13}$, independently, are a phenyl group, or an alkyl group having 1 to 10 carbon atoms, or wherein $R^{12}$ and $R^{13}$ are part of a cyclic ring.

13. A composition according to claim 12, wherein each said polymer repeat unit is derived from alkyl acrylate, vinyl acetate, acrylic acid, styrene, N-vinyl pyrrolidone or a combination thereof.

14. A composition according to claim 13, wherein $R^{12}$ and $R^{13}$, independently, are a phenyl group or an alkyl group having 1 to 10 carbon atoms, or $R^{12}$ and $R^{13}$ are part of a cyclic ring, and wherein $R^{14}$ is said alkyl having from 1 to about 12 carbon atoms or said aryl group.

15. A composition according to claim 14, wherein $R^{12}$ and $R^{13}$, independently, are a phenyl group or an alkyl group having from 1 to 8 carbon atoms.

16. A composition according to claim 15, wherein $R^{12}$ and $R^{13}$ independently, are an alkyl having from 1 to 4 carbon atoms, or are part of a cyclic ring.

17. A composition according to claim 16, wherein "a" is 2, and wherein $R^{12}$ and $R^{13}$, independently, are a phenyl group or alkyl group having 1 to 10 carbon atoms, or $R^{12}$ and $R^{13}$ are part of a cyclic ring.

18. A composition according to claim 11 wherein "a" is 2 to about 4.

19. A composition according to claim 18 wherein "a" is 2.

20. A composition, comprising:
a free radically polymerizable monomer selected from at least one conjugated diene monomer having 4 to 12 carbon atoms, at least one vinyl monomer, and combinations thereof,
wherein said at least one vinyl monomer is represented by the formula:

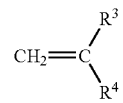

wherein $R^3$ is selected from hydrogen, halogen. $C_1$–$C_4$ alkyl, or substituted $C_1$–$C_4$ alkyl, wherein said substituents, independently, are selected from one or more hydroxy, alkoxy, aryloxy($OR^5$), carboxy, acyloxy, aroyloxy($O_2CR^5$), alkoxy-carbonyl($CO_2R^5$), or aryloxy-carbonyl; N-pyrrolidonyl;

wherein $R^4$ is selected from hydrogen, $R^5$, $CO_2H$, $CO_2R^5$, $COR^5$, CN, $CONH_2$, $CONHR^5$, $O_2CR^5$, $OR^5$ or halogen; and wherein $R^5$ is selected from $C_1$–$C_{18}$ alkyl, substituted $C_1$–$C_{18}$ alkyl, $C_2$–$C_{18}$ alkenyl, aryl, aralkyl, or alkaryl, and wherein said substituents, independently, are selected from one or more epoxy, hydroxy, alkoxy, acyl, acyloxy, carboxy and salts thereof, sulfonic acid and salts thereof, alkoxy- or aryloxy-carbonyl, dicyanato, cyano, silyl, halo or dialkylamino; and an alkoxy dithiocarbonate compound having the formula:

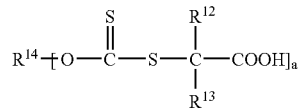

wherein $R^{12}$ and $R^{13}$, independently, can be the same or different, can be optionally substituted, can be a linear or branched alkyl having from 1 to 12 carbon atoms; or an aryl group having from 6 to 18 carbon atoms; or $R^{12}$ and $R^{13}$ can form or be a part of a substituted or unsubstituted cyclic ring having from 3 to 12 carbon atoms, wherein said substituted groups above are independently selected from alkyl having from 1 to 6 carbon atoms; an aryl group; a halogen; a cyano group; an ether having a total of from 2 to about 20 carbon atoms; a nitro; and combinations thereof;

wherein $R^{14}$ is optionally substituted, and can be a linear or branched alkyl having from 1 to about 12 carbon atoms, an aryl group optionally saturated or unsaturated; an arylalkyl having from about 7 to 18 carbon atoms; an acyl group; an alkene group; an alkenealkyl having from 3 to 18 carbon atoms; an alkylene group; an alkoxyalkyl; a polyalkylene glycol monoalkyl ether having from 3 to 200 carbon atoms; a polyalkylene glycol monoaryl ether having from 3 to 200 carbon atoms, a 2-trifluoroethyl group, wherein said substituted groups are selected from an alkyl having from 1 to 6 carbon atoms; an aryl; a halogen; a cyano group; an amino group; an alkene group; an alkoxycarbonyl group; an aryloxycarbonyl group; a carboxy group; an acyloxy group; a carbamoyl group; an alkylcarbonyl group; an alkylarylcarbonyl group; an arylcarbonyl group; an arylalkylcarbonyl group; a phtalimido group; a maleimido group; a succinimido group; an amidino group; a guanidimo group; an allyl group; an epoxy group; an alkoxy group; an alkali metal salt; a quaternary ammonium salt; a hydroxyl group; an ether having a total of from 2 to about 20 carbon atoms; a nitro group; a sulfur group; a phosphorous group; a carboalkoxy group; and combinations thereof; and wherein "a" is 1.

21. A composition according to claim 20, wherein $R^{12}$ and $R^{13}$, independently, are a phenyl group or an alkyl group having 1 to 10 carbon atoms, or wherein $R^{12}$ and $R^{13}$ are part of a cyclic ring.

22. A composition according to claim 20 wherein $R^{14}$ is an alkyl having from 1 to about 8 atoms.

23. A composition according to claim 20, wherein $R^{12}$ and $R^{13}$, independently, are a phenyl group, or an alkyl group having 1 to 10 carbon atoms, or wherein $R^{12}$ and $R^{13}$ are part of a cyclic ring, and wherein $R^{14}$ is an alkyl having from 1 to 8 carbon atoms.

24. A composition according to claim 21, wherein $R^{14}$ is an alkyl having from 1 to 4 carbon atoms.

* * * * *